US010221150B2

(12) United States Patent
Farmer et al.

(10) Patent No.: US 10,221,150 B2
(45) Date of Patent: Mar. 5, 2019

(54) CONTINUOUS CARBONYLATION PROCESSES

(71) Applicant: Novomer, Inc., Boston, MA (US)

(72) Inventors: Jay J. Farmer, Boston, MA (US); Peter Galebach, Madison, WI (US); Kyle Sherry, Rochester, NY (US); Sadesh H. Sookraj, Cambridge, MA (US)

(73) Assignee: Novomer, Inc., Boston, MA (US)

( * ) Notice: Subject to any disclaimer, the term of this patent is extended or adjusted under 35 U.S.C. 154(b) by 0 days.

(21) Appl. No.: 15/550,217

(22) PCT Filed: Feb. 12, 2016

(86) PCT No.: PCT/US2016/017875
§ 371 (c)(1),
(2) Date: Aug. 10, 2017

(87) PCT Pub. No.: WO2016/130998
PCT Pub. Date: Aug. 18, 2016

(65) Prior Publication Data
US 2018/0030015 A1 Feb. 1, 2018

Related U.S. Application Data

(60) Provisional application No. 62/116,089, filed on Feb. 13, 2015.

(51) Int. Cl.
C07D 307/60 (2006.01)
C07C 67/37 (2006.01)
B01J 31/00 (2006.01)
C07D 305/12 (2006.01)

(52) U.S. Cl.
CPC ............ C07D 307/60 (2013.01); B01J 31/00 (2013.01); C07C 67/37 (2013.01); C07D 305/12 (2013.01)

(58) Field of Classification Search
CPC ...... C07D 307/60; C07D 305/12; C07C 67/37
USPC ........................................................ 549/233
See application file for complete search history.

(56) References Cited

U.S. PATENT DOCUMENTS

| 2,245,404 | A | 6/1941 | Kise et al. |
| 2,302,321 | A | 11/1942 | Hopff et al. |
| 2,469,704 | A | 5/1949 | Stone |
| 2,526,554 | A | 10/1950 | Gresham et al. |
| 3,002,017 | A | 9/1961 | Wearsch et al. |
| 3,326,938 | A | 6/1967 | Lyle |
| 3,418,338 | A | 12/1968 | Gilman et al. |
| 3,751,435 | A | 8/1973 | Van Der Ven et al. |
| 3,800,006 | A | 3/1974 | Katayama et al. |
| 4,026,967 | A | 5/1977 | Flexman, Jr. et al. |
| 4,081,253 | A | 3/1978 | Marion |
| 4,221,727 | A | 9/1980 | Tsang et al. |
| 4,590,293 | A | 5/1986 | Pascoe |
| 4,873,378 | A | 10/1989 | Murphy et al. |
| 5,096,470 | A | 3/1992 | Krishnamurthy |
| 5,198,578 | A | 3/1993 | Etzkorn et al. |
| 5,705,688 | A | 1/1998 | Fauconet et al. |
| 5,731,252 | A | 3/1998 | Warner et al. |
| 6,123,812 | A | 9/2000 | Bessling et al. |
| 6,147,126 | A | 11/2000 | DeGeorge et al. |
| 6,348,611 | B1 | 2/2002 | Lee et al. |
| 6,392,078 | B1 | 5/2002 | Ryu et al. |
| 6,492,535 | B1 | 12/2002 | Castiglioni et al. |
| 6,541,665 | B1 | 4/2003 | Bastiaensen et al. |
| 6,573,340 | B1 | 6/2003 | Khemani et al. |
| 6,773,578 | B1 | 8/2004 | O'Rear et al. |
| 6,852,865 | B2 | 2/2005 | Coates et al. |
| 6,916,951 | B2 | 7/2005 | Tustin et al. |
| 8,277,660 | B2 | 10/2012 | Kimball et al. |
| 8,445,703 | B2 | 5/2013 | Allen et al. |
| 8,796,475 | B2 | 8/2014 | Allen et al. |
| 9,096,510 | B2 | 8/2015 | Porcelli et al. |
| 9,156,803 | B2 | 10/2015 | Allen et al. |
| 9,206,144 | B2 | 12/2015 | Allen et al. |
| 9,327,280 | B2 | 5/2016 | Lee et al. |
| 9,403,788 | B2 | 8/2016 | Lee et al. |
| 9,493,391 | B2 | 11/2016 | Allen et al. |
| 9,914,689 | B2 | 3/2018 | Porcelli et al. |
| 2003/0098274 | A1 | 5/2003 | Lee et al. |
| 2003/0162961 | A1 | 8/2003 | Coates et al. |
| 2004/0102532 | A1 | 5/2004 | Landis et al. |
| 2005/0014977 | A1 | 1/2005 | Drent et al. |
| 2005/0196343 | A1 | 9/2005 | Reddy et al. |

(Continued)

FOREIGN PATENT DOCUMENTS

CN 103822811 A 5/2014
EP 0352850 A1 1/1990
(Continued)

OTHER PUBLICATIONS

International Preliminary Report on Patentability received for PCT Patent Application No. PCT/US2016/017875, dated Aug. 24, 2017, 9 pages.
International Search Report and Written Opinion for PCT Patent Application No. PCT/US2016/017875 dated May 6, 2016, 16 Pages.
Ganji et al., "In Situ Generation of the Coates Catalyst: A Practical and Versatile Catalytic System for the Carbonylation of Meso-Epoxides", Organic Letters, vol. 13, No. 12, 2011, pp. 3142-3145.
Ganji et al., "In Situ Generation of the Coates Catalyst: a Practical and Versatile Catalytic System for the Carbonylation of Meso-Epoxides", Cheminform Abstract, vol. 42, No. 39, 2011, 1 page.

(Continued)

Primary Examiner — Taylor V Oh
(74) Attorney, Agent, or Firm — Morrison & Foerster LLP

(57) ABSTRACT

Provided are processes for monitoring and maintaining continuous carbonylation of epoxides or lactones. Processes include measuring parameters affecting the rate of the carbonylation reaction and adding supplemental replacement catalyst replacement components to maintain a constant rate of carbonylation.

31 Claims, No Drawings

(56) References Cited

U.S. PATENT DOCUMENTS

| | | |
|---|---|---|
| 2005/0209411 A1 | 9/2005 | Nestler et al. |
| 2005/0222458 A1 | 10/2005 | Craciun et al. |
| 2005/0240032 A1 | 10/2005 | Luinstra et al. |
| 2005/0256320 A1* | 11/2005 | Luinstra ............... B01J 31/122 549/328 |
| 2006/0189833 A1 | 8/2006 | Powell et al. |
| 2007/0155984 A1 | 7/2007 | Sielcken et al. |
| 2007/0217965 A1 | 9/2007 | Johnson et al. |
| 2007/0225522 A1 | 9/2007 | Kobayashi et al. |
| 2007/0293695 A1 | 12/2007 | Zoeller et al. |
| 2009/0075295 A1 | 3/2009 | Lindsey |
| 2009/0124787 A1 | 5/2009 | Preishuber-Pflugl et al. |
| 2009/0173694 A1 | 7/2009 | Peinemann et al. |
| 2009/0178495 A1 | 7/2009 | Steigmiller et al. |
| 2009/0253934 A1 | 10/2009 | Ho et al. |
| 2009/0287000 A1 | 11/2009 | Coates et al. |
| 2009/0287280 A1 | 11/2009 | Wong et al. |
| 2009/0299032 A1 | 12/2009 | Allen |
| 2010/0323573 A1 | 12/2010 | Chu et al. |
| 2010/0323885 A1 | 12/2010 | Herfert et al. |
| 2011/0065894 A1 | 3/2011 | Allen |
| 2011/0226697 A1 | 9/2011 | McLellan et al. |
| 2011/0301027 A1 | 12/2011 | Bitis et al. |
| 2011/0319849 A1 | 12/2011 | Collias et al. |
| 2012/0108695 A1 | 5/2012 | Won et al. |
| 2012/0123137 A1 | 5/2012 | Allen et al. |
| 2012/0189861 A1 | 7/2012 | Matsumoto et al. |
| 2012/0202951 A1 | 8/2012 | Gartner et al. |
| 2013/0004454 A1 | 1/2013 | Weiss et al. |
| 2013/0072645 A1 | 3/2013 | Balduf et al. |
| 2013/0165670 A1 | 6/2013 | Allen et al. |
| 2013/0274697 A1 | 10/2013 | Godlewski et al. |
| 2013/0281715 A1 | 10/2013 | Allen et al. |
| 2013/0299417 A1 | 11/2013 | Luchinger et al. |
| 2014/0018570 A1 | 1/2014 | Pazicky et al. |
| 2014/0018574 A1 | 1/2014 | Raith et al. |
| 2014/0221702 A1 | 8/2014 | Weston et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0141693 A1 | 5/2015 | Allen et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0204465 A1 | 7/2016 | Mimura et al. |
| 2016/0288057 A1 | 10/2016 | Lapointe et al. |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030201 A1 | 2/2018 | Farmer et al. |
| 2018/0057619 A1 | 3/2018 | Sookraj |
| 2018/0094100 A1 | 4/2018 | Farmer et al. |

FOREIGN PATENT DOCUMENTS

| | | |
|---|---|---|
| EP | 0441447 A1 | 8/1991 |
| EP | 2325214 A1 | 5/2011 |
| GB | 5762138 A | 11/1956 |
| JP | 57-14596 A | 1/1982 |
| WO | 2002/09781 A2 | 2/2002 |
| WO | 2006/087556 A1 | 8/2006 |
| WO | 2010/118128 A1 | 10/2010 |
| WO | 2010/137974 A1 | 12/2010 |
| WO | 2011/123558 A1 | 10/2011 |
| WO | 2011/163309 A2 | 12/2011 |
| WO | 2012/030619 A1 | 3/2012 |
| WO | 2012/158573 A1 | 11/2012 |
| WO | 2013/063191 A1 | 5/2013 |
| WO | 2013/067460 A1 | 5/2013 |
| WO | 2013/068846 A1 | 5/2013 |
| WO | 2013/122905 A1 | 8/2013 |
| WO | 2013/126375 A1 | 8/2013 |
| WO | 2013/180659 A1 | 12/2013 |
| WO | 2013/185009 A1 | 12/2013 |
| WO | 2014/004858 A1 | 1/2014 |
| WO | 2014/008232 A2 | 1/2014 |
| WO | 2015/085295 A2 | 6/2015 |
| WO | 2015/110321 A1 | 7/2015 |
| WO | 2015/138975 A1 | 9/2015 |
| WO | 2015/171382 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165344 A1 | 9/2017 |
| WO | 2017/165345 A1 | 9/2017 |
| WO | 2018/085251 A1 | 5/2018 |
| WO | 2018/085254 A1 | 5/2018 |
| WO | 2018/136638 A1 | 7/2018 |
| WO | 2018/170006 A1 | 9/2018 |

OTHER PUBLICATIONS

Getzler et al., "Synthesis of β-Lactones: A Highly Active and Selective Catalyst for Epoxide Carbonylation" Journal of the American Chemical Society. vol. 124, No. 7, 2002, pp. 1174-1175.

International Search Report and Written Opinion received for PCT Patent Application PCT/US11/49125, dated Jan. 11, 2012, 10 pages.

International Search Report and Written Opinion received for PCT Patent Application No. PCT/US13/25683, dated Apr. 23, 2013, 8 pages.

International Search Report and Written Opinion received for PCT Patent Application No. PCT/US17/23302, dated Jun. 5, 2017, 9 pages.

International Search Report and Written Opinion received for PCT Patent Application No. PCT/US17/23303, dated Jun. 7, 2017, 18 pages.

International Search Report and Written Opinion received for PCT Patent Application No. PCT/US2010/030230, dated Jun. 10, 2010, 17 pages.

International Search Report and Written Opinion received for PCT Patent Application No. PCT/US2012/061791, dated Feb. 8, 2013, 10 pages.

International Search Report and Written Opinion received for PCT Patent Application No. PCT/US2013/026810, dated Apr. 30, 2013, 8 pages.

International Search Report and Written Opinion received for PCT Patent Application No. PCT/US2013/048238, dated Dec. 3, 2013, 8 pages.

International Search Report and Written Opinion received for PCT Patent Application No. PCT/US2013/049026, dated Dec. 17, 2013, 9 pages.

International Search Report and Written Opinion received for PCT Patent Application No. PCT/US2014/069066, dated Mar. 16, 2015, 10 pages.

International Search Report and Written Opinion received for PCT Patent Application No. PCT/US2015/020562, dated Jun. 18, 2015, 9 pages.

(56) References Cited

OTHER PUBLICATIONS

International Search Report and Written Opinion received for PCT Patent Application No. PCT/US2015/028123, dated Jul. 23, 2015, 7 pages.
International Search Report and Written Opinion received for PCT Patent Application No. PCT/US2015/033232, dated Aug. 19, 2015, 8 pages.
International Search Report and Written Opinion received for PCT Patent Application No. PCT/US2015/042124, dated Dec. 15, 2015, 14 pages.
International Search Report and Written Opinion received for PCT Patent Application No. PCT/US2016/017797, dated May 5, 2016, 9 pages.
International Search Report and Written Opinion received for PCT Patent Application No. PCT/US2016/017844, dated May 6, 2016, 10 pages.
International Search Report and Written Opinion received for PCT Patent Application No. PCT/US2016/017861, dated Apr. 29, 2016, 25 pages.
International Search Report and Written Opinion received for PCT Patent Application No. PCT/US2016/017868, dated May 2, 2016, 9 pages.
International Search Report and Written Opinion received for PCT Patent Application No. PCT/US2016/017878, dated May 2, 2016, 9 pages.
International Search Report and Written Opinion received for PCT Patent Application No. PCT/US2016/017880, dated Apr. 29, 2016, 9 pages.
International Search Report and Written Opinion received for PCT Patent Application No. PCT/US2016/017881, dated May 2, 2016, 8 pages.
International Search Report and Written Opinion received for PCT Patent Application No. PCT/US2016/044772, dated Nov. 8, 2016, 17 pages.
International Search Report and Written Opinion received for PCT Patent Application No. PCT/US2016/044927, dated Nov. 8, 2016, 17 pages.
International Search Report and Written Opinion received for PCT Patent Application No. PCT/US2017/059243, dated Feb. 1, 2018, 10 pages.
International Search Report and Written Opinion received for PCT Patent Application No. PCT/US2017/059249, dated Feb. 22, 2018, 11 pages.
International Search Report and Written Opinion received for PCT Patent Application No. PCT/US2018/014243, dated Mar. 28, 2018, 11 pages.
International Search Report and Written Opinion received for PCT Patent Application No. PCT/US2012/037675, dated Aug. 9, 2012, 12 pages.
Rowley et al., "Catalytic Double Carbonylation of Epoxides to Succinic Anhydrides: Catalyst Discovery, Reaction Scope, and Mechanism", Journal of the American Chemical Society, vol. 129, No. 16, 2007, pp. 4948-4960.
Slowik et al., "Catalytic Conversion of Waste Carbon Monoxide to Valuable Chemicals & Materials", Clean Technology, 2010, pp. 283-286.
Stanghellini et al., "Redox Reactions of Metal Carbonyls. I. Kinetics and Mechanism of Disproportionation of $CO_2(CO)_8$ with Piperidine", Inorganica Chimica Acta, vol. 22, 1977, pp. 19-22.
Trimm, D. L., "Minimisation of Carbon Monoxide in a Hydrogen Stream for Fuel Cell Application", Applied Catalysis A: General, vol. 296, 2005, 11 pages.
"Understanding Biobased Carbon Content", Society of the Plastics Industry Bioplastics Council, Feb. 2012, pp. 1-12.
Church et al., "The Mechanism of Epoxide Carbonylation by [Lewis Acid]+[Co(CO)$_4$]-Catalysts", J. Am. Chem. Soc., vol. 128, No. 31, 2006, pp. 10125-10133.
Extended European Search Report (includes Supplementary European Search Report and European Search Opinion) received for European Patent Application No. 16750021.4, dated Jun. 27, 2018, 8 pages.

\* cited by examiner

CONTINUOUS CARBONYLATION PROCESSES

CROSS-REFERENCE TO RELATED APPLICATIONS

This application is a U.S. National Phase Patent Application of PCT/US2016/017875, filed Feb. 12, 2016, which claims priority to and the benefit of U.S. Provisional Patent Application No. 62/116,089, filed Feb. 13, 2015, each of which is incorporated herein by reference in its entirety.

FIELD

The present disclosure relates generally to a carbonylation reaction, and more specifically to the continuous carbonylation of an epoxide or lactone feedstock.

BACKGROUND

Bimetallic complexes containing a Lewis acid in combination with metal carbonyl are highly active catalysts for the ring-expanding carbonylation of strained heterocycles, including epoxides, aziridines, oxetanes and lactones. In particular, such bimetallic catalysts comprising a cationic aluminum complex as a Lewis-acidic component and a carbonyl cobaltate anion are useful for the mono- and bis-carbonylation of epoxides to form beta-lactones and succinic anhydrides respectively (Rowley et al., *J. Am. Chem. Soc.*, 2007, 129, 4948-4960).

Continuous production of these beta-lactones and succinic anhydrides is possible by the continuous addition of epoxide and carbon monoxide feedstocks, and the continuous removal of the beta-lactone or succinic anhydride products. However, the carbonylation catalysts used for these reactions have a limited effective lifespan, and accordingly, the continuous production of carbonylation products slows down over time or ceases entirely once the active catalyst species is no longer present to catalyze the reaction. These active catalysts are expensive, so the addition of a whole new amount of active catalyst is not economically preferable.

Furthermore, many of the active catalysts are air sensitive and it is undesirable to have to produce and handle them in a separate step prior to adding them to the continuous carbonylation reactor. Such a separate step can be problematic at commercial production volumes. As such, there remains a need for methods of maintaining effective amounts of carbonylation catalysts in a continuous carbonylation reactor that are practical and efficient for large-scale use.

BRIEF SUMMARY

In one aspect, provided is a process for continuous carbonylation of an epoxide or lactone feedstock, comprising:
reacting an epoxide or lactone feedstock with carbon monoxide in the presence of a catalyst comprising a Lewis acid and a metal carbonyl in a carbonylation reaction vessel;
measuring one or more parameters selected from the group consisting of:
  i) a concentration of the Lewis acid, or a decomposition product thereof, within the carbonylation reaction vessel;
  ii) a concentration of the Lewis acid, or a decomposition product thereof, in a product stream downstream from the carbonylation reaction vessel;
  iii) a concentration of the metal carbonyl, or a decomposition product thereof, within the carbonylation reaction vessel;
  iv) a concentration of the metal carbonyl, or a decomposition product thereof, in a product stream downstream from the carbonylation reaction vessel; and
  v) a rate of the carbonylation reaction;
comparing the measured value of the one or more parameters to predetermined reference values for the one or more parameters; and
where the measured value of any one of parameters i), iii), or v) is less than the reference value, or where the measured value of any one of parameters ii) or iv) is greater than the reference value, introducing to the carbonylation reaction vessel a catalyst replacement component which is different from the catalyst and comprises a species selected from the group consisting of the Lewis acid, a precursor to the Lewis acid, the metal carbonyl, and a precursor to the metal carbonyl.

In another aspect, provided is a process for continuous carbonylation of an epoxide or lactone feedstock, comprising:
continuously reacting an epoxide or lactone feedstock with carbon monoxide in the presence of a carbonylation catalyst in a carbonylation reaction vessel,
  wherein the carbonylation catalyst comprises a Lewis acid and a metal carbonyl, and
  wherein at a start time of the process, the carbonylation reaction vessel contains an initial concentration of the Lewis acid and an initial concentration of the metal carbonyl; and
adding to the carbonylation reaction vessel, at a time after the start time of the process, a catalyst replacement component which is different from the catalyst,
  wherein the catalyst replacement component comprises the Lewis acid, a precursor to the Lewis acid, the metal carbonyl, and a precursor to the metal carbonyl.

In some variations of the foregoing aspect, a rate or time of addition of the catalyst replacement component is based on a rate of depletion of one or both of the Lewis acid and the metal carbonyl in the carbonylation reaction vessel.

In another aspect, provided is a process for continuous carbonylation of an epoxide or lactone feedstock, comprising:
reacting an epoxide or lactone feedstock with carbon monoxide in the presence of a catalyst in a carbonylation reaction vessel, wherein the catalyst comprises a Lewis acid and a metal carbonyl; and
continuously or intermittently introducing to the carbonylation reaction vessel a catalyst replacement component which is different from the catalyst, wherein the catalyst replacement component comprises a species selected from the group consisting of the Lewis acid, a precursor to the Lewis acid, the metal carbonyl, and a precursor to the metal carbonyl.

In some embodiments, the Lewis acids, decomposition products of Lewis acids, precursors to the Lewis acids, metal carbonyls, decomposition products of metal carbonyls, and precursors to the metal carbonyls include those described in classes and subclasses herein.

Definitions

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. In some variations, the aliphatic group is unbranched or branched. In other variations, the aliphatic group is cyclic. Unless otherwise specified, in some variations, aliphatic groups contain 1-30 carbon atoms. In some embodiments, aliphatic groups contain 1-12 carbon atoms. In some embodiments, aliphatic groups contain 1-8 carbon atoms. In some embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, for example, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In some embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups. In some variations, the heteroaliphatic group is branched or unbranched. In other variations, the heteroaliphatic group is cyclic. In yet other variations, the heteroaliphatic group is acyclic.

In some variations, the term "epoxide", as used herein, refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted as defined herein. In some embodiments, epoxides comprise a single oxirane moiety. In some embodiments, epoxides comprise two or more oxirane moieties.

In some variations, the term "glycidyl", as used herein, refers to an oxirane substituted with a hydroxyl methyl group or a derivative thereof. In other variations, the term glycidyl as used herein is meant to include moieties having additional substitution on one or more of the carbon atoms of the oxirane ring or on the methylene group of the hydroxymethyl moiety, examples of such substitution may include, for example, alkyl groups, halogen atoms, and aryl groups. The terms glycidyl ester, glycidyl acrylate, and glydidyl ether denote substitution at the oxygen atom of the above-mentioned hydroxymethyl group. For example, the oxygen atom is bonded to an acyl group, an acrylate group, or an alkyl group respectively.

The term "acrylate" or "acrylates" as used herein refer to any acyl group having a vinyl group adjacent to the acyl carbonyl. The terms encompass mono-, di- and tri-substituted vinyl groups. Acrylates may include, for example, acrylate, methacrylate, ethacrylate, cinnamate (3-phenylacrylate), crotonate, tiglate, and senecioate.

The terms "crude acrylic acid" and "glacial acrylic acid", as used herein, describe acrylic acid of relatively low and high purity, respectively. Crude acrylic acid (also called technical grade acrylic acid) has a typical minimum overall purity level of 94% and can be used to make acrylic esters for paint, adhesive, textile, paper, leather, fiber, and plastic additive applications. Glacial acrylic acid has a typical overall purity level ranging from 98% to 99.99% and can be used to make polyacrylic acid for superabsorbent polymers (SAPs) in disposable diapers, training pants, adult incontinence undergarments and sanitary napkins. Polyacrylic acid (PAA) is also used in compositions for paper and water treatment, and in detergent co-builder applications. In some variations, acrylic acid has a purity of at least 98%, at least 98.5%, at least 99%, at least 99.1%, at least 99.2%, at least 99.3%, at least 99.4%, at least 99.5%, at least 99.6%, at least 99.7%, at least 99.8%, or at least 99.9%; or between 99% and 99.95%, between 99.5% and 99.95%, between 99.6% and 99.95%, between 99.7% and 99.95%, or between 99.8% and 99.95%.

Suitable salts of PAA include metal salts, such those of any alkali (e.g., $Na^+$, $K^+$) cations, alkaline earth cations. In certain embodiments, the PAA salt is the $Na^+$ salt, i.e., sodium PAA. In certain embodiments, the salt is the $K^+$ salt, i.e., potassium PAA.

Impurities in glacial acrylic acid are reduced to an extent possible to facilitate a high-degree of polymerization to acrylic acid polymers (PAA) and avoid adverse effects from side products in end applications. For example, aldehyde impurities in acrylic acid hinder polymerization and may discolor the polymerized acrylic acid. Maleic anhydride impurities form undesirable copolymers which may be detrimental to polymer properties. Carboxylic acids, e.g., saturated carboxylic acids that do not participate in the polymerization, can affect the final odor of PAA or SAP-containing products and/or detract from their use. For example, foul odors may emanate from SAP that contains acetic acid or propionic acid and skin irritation may result from SAP that contains formic acid.

The reduction or removal of impurities from petroleum-based acrylic acid is costly, whether to produce petroleum-based crude acrylic acid or petroleum-based glacial acrylic acid. Such costly multistage distillations and/or extraction and/or crystallizations steps are generally employed (e.g., as described in U.S. Pat. Nos. 5,705,688 and 6,541,665).

The term "polymer", as used herein, refers to a molecule comprising multiple repeating units. In some variations, the polymer is a molecule of high relative molecular mass, the structure of which comprises the multiple repetition of units derived, actually or conceptually, from molecules of low relative molecular mass. In some embodiments, a polymer is comprised of only one monomer species (e.g., polyethylene oxide). In some embodiments, the polymer may be a copolymer, terpolymer, heteropolymer, block copolymer, or tapered heteropolymer of one or more epoxides. In one variation, the polymer may be a copolymer, terpolymer, heteropolymer, block copolymer, or tapered heteropolymer of two or more monomers.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, for example, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic.

The term "alkyl," as used herein, refers to a saturated hydrocarbon radical. In some variations, the alkyl group is a saturated, straight- or branched-chain hydrocarbon radicals derived from an aliphatic moiety containing between one and six carbon atoms by removal of a single hydrogen atom. Unless otherwise specified, in some variations, alkyl groups contain 1-12 carbon atoms. In some embodiments, alkyl groups contain 1-8 carbon atoms. In some embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Alkyl radicals may include, for example to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, and dodecyl.

The term "alkenyl," as used herein, denotes a monovalent group having at least one carbon-carbon double bond. In some variations, the alkenyl group is a monovalent group derived from a straight- or branched-chain aliphatic moiety having at least one carbon-carbon double bond by the removal of a single hydrogen atom. Unless otherwise specified, in some variations, alkenyl groups contain 2-12 carbon atoms. In some embodiments, alkenyl groups contain 2-8 carbon atoms. In some embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, and 1-methyl-2-buten-1-yl.

The term "alkynyl," as used herein, refers to a monovalent group having at least one carbon-carbon triple bond. In some variations, the alkynyl group is a monovalent group derived from a straight- or branched-chain aliphatic moiety having at least one carbon-carbon triple bond by the removal of a single hydrogen atom. Unless otherwise specified, in some variations, alkynyl groups contain 2-12 carbon atoms. In some embodiments, alkynyl groups contain 2-8 carbon atoms. In some embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, for example ethynyl, 2-propynyl (propargyl), and 1-propynyl.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include, for example, cyclopropane, cyclobutane, cyclopentane, cyclohexane, bicyclo[2,2,1]heptane, norbornene, phenyl, cyclohexene, naphthalene, and spiro[4.5]decane.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In some embodiments, "aryl" refers to an aromatic ring system which includes, for example, phenyl, naphthyl, and anthracyl, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, and tetrahydronaphthyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 pi ($\pi$) electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and may be saturated or partially unsaturated, and have, in addition to carbon atoms, one or more, preferably one to four, heteroatoms, as defined above. In some variations, the heterocyclic group is a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, for example, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds described herein may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned are preferably those that result in the formation of stable or chemically feasible compounds. The term "stable", as used herein, refers to compounds that are not substantially altered when subjected to conditions to allow for their production, detection, and, in some embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)N(R°)_2$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$; —SC(S)SR°; —$(CH_2)_{0-4}SC(O)R°$; —$(CH_2)_{0-4}C(O)NR°_2$; —$C(S)NR°_2$; —C(S)SR°; —SC(S)SR°, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched)alkylene)O—$N(R°)_2$; or —$(C_{1-4}$ straight or branched)alkylene)C(O)O—$N(R°)_2$, wherein each R° may be substituted as defined below and is independently hydrogen, $C_{1-8}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl mono- or polycyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —O(haloR$^●$), —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-4}C(O)N(R°)_2$; —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene)C(O)OR$^●$, or —SSR$^●$ wherein each R$^●$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}_2$, or —NO$_2$, wherein each R$^{\bullet}$ is unsubstituted or where preceded by "halo" is substituted only with one or more halogens, and is independently C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include —R$^{\dagger}$, —NR$^{\dagger}_2$, —C(O)R$^{\dagger}$, —C(O)OR$^{\dagger}$, —C(O)C(O)R$^{\dagger}$, —C(O)CH$_2$C(O)R$^{\dagger}$, —S(O)$_2$R$^{\dagger}$, —S(O)$_2$NR$^{\dagger}_2$, —C(S)NR$^{\dagger}_2$, —C(NH)NR$^{\dagger}_2$, or —N(R$^{\dagger}$)S(O)$_2$R$^{\dagger}$; wherein each R$^{\dagger}$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^{\bullet}$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^{\dagger}$ are independently halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}_2$, or —NO$_2$, wherein each R$^{\bullet}$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "catalyst" refers to a substance the presence of which increases the rate of a chemical reaction, while not being consumed or undergoing a permanent chemical change itself.

"Tetradentate" refers to ligands having four sites capable of coordinating to a single metal center.

As used herein, the term "about" preceding one or more numerical values means the numerical value ±5%. It should be understood that reference to "about" a value or parameter herein includes (and describes) embodiments that are directed to that value or parameter per se. For example, description referring to "about x" includes description of "x" per se.

DETAILED DESCRIPTION

Provided herein are carbonylation methods that employ a two-component catalyst system comprising a Lewis acid and a metal carbonyl. In some aspects, such methods are a continuous carbonylation process wherein epoxides and carbon monoxide are fed in, and carbonylation reaction products are continuously produced. The methods described herein solve a problem associated with continuous carbonylation processes, whereby over the course of time, one component of the two-component catalyst system is depleted at a faster rate than the other. As both components of the two-component catalyst system are required to effect the carbonylation reaction, the overall carbonylation reaction rate decreases with the decrease in concentration of the least plentiful component.

In some embodiments, particularly where the product stream is separated from the carbonylation reaction vessel by a nanofiltration membrane, one or both components of the catalyst have unexpectedly been observed to pass through the nanofiltration membrane. This observation is unexpected since the nanofiltration membrane is specifically selected to retain both components of the two-component catalyst, while allowing the carbonylation reaction products to pass. In some embodiments, the methods described herein restore proper balance between the components of the two-component catalyst by supplementation with the depleted catalyst components, in the form of catalyst replacement components.

In some embodiments, one or both of the components of the two-component catalyst are decomposed by exposure to trace quantities of oxygen, water, or other external contaminants, despite careful measures to exclude them. This results in decomposition products of the catalyst persisting in the carbonylation reaction vessel or passing into the product stream. In one embodiment, the decomposition products can be combined with catalyst replacement components to regenerate the active catalyst components without the need to add entirely new portions of catalyst. In some embodiments, where the decomposition products persist in the carbonylation reaction vessel, the addition of the catalyst replacement components results in the in situ regeneration of the active two-component catalyst. In some embodiments, where the decomposition products pass into the product stream, they may be isolated from the product stream and combined with the catalyst replacement components (either in situ or ex situ) to regenerate the active two-component catalyst.

In some embodiments, one or both components of the catalyst passes into the product stream, and one or both components are decomposed.

I. Process for Monitoring and Replacing Catalyst

In one aspect, provided is a process for continuous carbonylation of an epoxide or lactone feedstock, comprising:

reacting an epoxide or lactone feedstock with carbon monoxide in the presence of a catalyst comprising a Lewis acid and a metal carbonyl in a carbonylation reaction vessel;

measuring one or more parameters selected from the group consisting of:
  i) a concentration of the Lewis acid, or a decomposition product thereof, within the carbonylation reaction vessel;
  ii) a concentration of the Lewis acid, or a decomposition product thereof, in a product stream downstream from the carbonylation reaction vessel;
  iii) a concentration of the metal carbonyl, or a decomposition product thereof, within the carbonylation reaction vessel;
  iv) a concentration of the metal carbonyl, or a decomposition product thereof, in a product stream downstream from the carbonylation reaction vessel; and
  v) a rate of the carbonylation reaction;

comparing the measured value of the one or more parameters to predetermined reference values for the one or more parameters; and where the measured value of any one of parameters i), iii), or v) is less than the reference value, or where the measured value of any one of parameters ii) or iv) is greater than the reference value, introducing to the carbonylation reaction vessel a catalyst replacement component which is different from the catalyst and comprises a species selected from the group consisting of the Lewis acid, a precursor to the Lewis acid, the metal carbonyl, and a precursor to the metal carbonyl.

In some embodiments, one of the one or more parameters measured is the concentration of the Lewis acid, or a decomposition product thereof, within the carbonylation reaction vessel. In some embodiments, the concentration of the Lewis acid within the carbonylation reaction vessel is measured. In some embodiments, the concentration of a decomposition product of the Lewis acid within the carbonylation reaction vessel is measured.

In some embodiments, one of the one or more parameters measured is the concentration of the metal carbonyl, or a decomposition product thereof, within the carbonylation reaction vessel. In some embodiments, the concentration of the metal carbonyl within the carbonylation reaction vessel is measured. In some embodiments, the concentration of a decomposition product of the metal carbonyl within the carbonylation reaction vessel is measured.

In some embodiments, one of the one or more parameters measured is the concentration of the Lewis acid, or a decomposition product thereof, in the product stream downstream from the carbonylation reaction vessel. In some embodiments, the concentration of the Lewis acid in the product stream downstream from the carbonylation reaction vessel is measured. In some embodiments, the concentration of a decomposition product of the Lewis acid in the product stream downstream from the carbonylation reaction vessel is measured.

In some embodiments, one of the one or more parameters measured is the concentration of the metal carbonyl, or a decomposition product thereof, in the product stream downstream from the carbonylation reaction vessel. In some embodiments, the concentration of the metal carbonyl in the product stream downstream from the carbonylation reaction vessel is measured. In some embodiments, the concentration of a decomposition product of the metal carbonyl in the product stream downstream from the carbonylation reaction vessel is measured.

In some embodiments, one of the one or more parameters measured is the rate of the carbonylation reaction. In some embodiments, the rate of the carbonylation reaction is measured by the change in concentration of a carbonylation product in the carbonylation reaction vessel over time. In some embodiments, the rate of the carbonylation reaction is measured by the change in concentration of a carbonylation product in the product stream downstream from the carbonylation reaction vessel over time.

In other aspects, provided is a process for continuous carbonylation of an epoxide or lactone feedstock, comprising:
  continuously reacting an epoxide or lactone feedstock with carbon monoxide in the presence of a carbonylation catalyst in a carbonylation reaction vessel,
    wherein the carbonylation catalyst comprises a Lewis acid and a metal carbonyl, and
    wherein at a start time of the process, the carbonylation reaction vessel contains an initial concentration of the Lewis acid and an initial concentration of the metal carbonyl; and
  adding to the carbonylation reaction vessel, at a time after the start time of the process, a catalyst replacement component which is different from the catalyst,
    wherein the catalyst replacement component comprises the Lewis acid, a precursor to the Lewis acid, the metal carbonyl, and a precursor to the metal carbonyl.

In some embodiments, a rate or time of addition of the catalyst replacement component is based on a rate of depletion of one or both of the Lewis acid and the metal carbonyl in the carbonylation reaction vessel. In some variations of the foregoing, one or both of the Lewis acid and the metal carbonyl of the carbonylation catalyst depletes over time in the carbonylation reaction vessel, and the method further comprises determining the depletion.

In certain embodiments of the foregoing, the depletion of one or both of the Lewis acid and the metal carbonyl in the carbonylation reaction vessel is determined by:
  measuring one or more parameters selected from the group consisting of:
    i-a) a concentration of the Lewis acid in the carbonylation reaction vessel;
    i-b) a concentration of a decomposition product of the Lewis acid in the carbonylation reaction vessel;
    ii-a) a concentration of the Lewis acid in a process stream downstream from the carbonylation reaction vessel;
    ii-b) a concentration of a decomposition product of the Lewis acid in a process stream downstream from the carbonylation reaction vessel;
    iii-a) a concentration of the metal carbonyl in the carbonylation reaction vessel;
    iii-b) a concentration of a decomposition product of the metal carbonyl in the carbonylation reaction vessel;
    iv-a) a concentration of the metal carbonyl in a process stream downstream from the carbonylation reaction vessel;
    iv-b) a concentration of a decomposition product of the metal carbonyl in a process stream downstream from the carbonylation reaction vessel; and
    v) a rate of the carbonylation reaction; and
  obtaining a measured value of the one or more parameters.

In some embodiments, the method further comprises:
  comparing the measured value of the one or more parameters to a predetermined reference value for each parameter; and
  determining a rate of addition or a time of addition of the catalyst replacement component based on the comparison.

In some variations, the rate of addition of the metal carbonyl or a precursor to the metal carbonyl is increased when the value of a measurement in parameter iii-b, iv-a, or iv-b, or any combination thereof, is greater than the predetermined value for each parameter. In some variations, the rate of addition of the metal carbonyl or a precursor to the metal carbonyl is increased when the value of a measurement in parameter iii-a is less than the predetermined value for the parameter. In other variations, the rate of addition of the Lewis acid or a precursor to the Lewis Acid is increased when the value of a measurement in parameter i-b, ii-a, or ii-b, or any combination thereof, is greater than the predetermined value for each parameter. In yet other variations, the rate of addition of the Lewis acid or a precursor to the Lewis acid is increased when the value of a measurement in parameter i-a is less than the predetermined value for the parameter.

In some embodiments, the product stream is separated from the carbonylation reaction vessel by a nanofiltration membrane. In some embodiments, the nanofiltration membrane is selected based on its ability to retain solutes having a molecular weight greater than the molecular weight of the epoxide or lactone carbonylation products, and to allow solutes having lower molecular weights to permeate.

In some embodiments, the catalyst replacement component comprises the Lewis acid, or a precursor to the Lewis acid. In some embodiments, the catalyst replacement component comprises the Lewis acid. In some embodiments, the catalyst replacement component comprises a precursor to the Lewis acid.

In some embodiments, the catalyst replacement component comprises the metal carbonyl, or a precursor to the metal carbonyl. In some embodiments, the catalyst replacement component comprises the metal carbonyl. In some embodiments, the catalyst replacement component comprises a precursor to the metal carbonyl.

In some embodiments, where more than one catalyst replacement component is added, each of the one or more catalyst replacement components is added to the carbonylation reaction vessel separately. In some embodiments, where more than one catalyst replacement component is added, all of the one or more catalyst replacement components are added to the carbonylation reaction vessel together.

In some embodiments, each of the one or more catalyst replacement components is added individually to the carbonylation reaction vessel without solvent, as a solution in an organic solvent, or as a slurry. In some embodiments, each of the one or more catalyst replacement components is added to the carbonylation reaction vessel without solvent. In some embodiments, each of the one or more catalyst replacement components is added to the carbonylation reaction vessel as a solution in an organic solvent. In some embodiments, each of the one or more catalyst replacement components is added to the carbonylation reaction vessel as a slurry.

In certain embodiments, where more than one catalyst replacement component are added, each catalyst replacement component is dissolved in solution, and the solutions are combined enroute to the vessel, e.g., by using a mixing tee or flowing the combined solutions through a static mixer.

In certain embodiments, fresh catalyst may also be added to the reaction vessel at the same or different times as the one or more catalyst replacement components.

In certain embodiments, the catalyst replacement components are added under an atmosphere comprising CO. In certain embodiments, the CO is present at a pressure from about 1 atmosphere to about 400 atmospheres. In certain embodiments, the catalyst replacement components are added under an atmosphere comprising CO at a pressure between about 1 atmosphere and about 100 atmospheres, or between about 1 atmosphere and about 50 atmospheres, or between about 10 atmospheres and about 20 atmospheres, or between about 5 atmospheres and about 10 atmospheres, or between about 1 atmosphere and about 5 atmospheres.

In some embodiments, the amount of a given catalyst replacement component added to the carbonylation reaction vessel is proportional to one of the parameters being measured in step (a). In some embodiments, the amount of a given catalyst replacement component is directly proportional to changes in the concentration of the parameter measured in the product stream downstream from the carbonylation reaction vessel.

In some embodiments, if the concentration of the Lewis acid, or a decomposition product thereof, measured in step (a) is increased in the product stream downstream from the carbonylation reaction vessel, an amount of Lewis acid that is proportional to the increase in the concentration of Lewis acid, or a decomposition product thereof, measured in step (a) is added to the carbonylation reaction vessel. In some embodiments, if the concentration of the Lewis acid, measured in step (a) is found to have decreased within the carbonylation reaction vessel, an amount of Lewis acid, or a precursor to the Lewis acid, that is proportional to the decrease in the concentration of Lewis acid, measured in step (a) is added to the carbonylation reaction vessel. For example, if the concentration of the Lewis acid has decreased by 5%, an amount of the Lewis acid or precursor to the Lewis acid that is equivalent to about 5% of the amount of the Lewis acid initially charged into the carbonylation reaction vessel is added. In some embodiments, if the concentration of a Lewis acid decomposition product, measured in step (a) is found to have increased within the carbonylation reaction vessel, an amount of Lewis acid, or a precursor to the Lewis acid, that is proportional to the increase in the concentration of Lewis acid decomposition product measured in step (a) is added to the carbonylation reaction vessel. For example, if the concentration of the Lewis acid decomposition product has increased to 5% of the original concentration of Lewis acid, an amount of the Lewis acid or precursor to the Lewis acid that is equivalent to about 5% of the amount of the Lewis acid initially charged into the carbonylation reaction vessel is added.

In some embodiments, if the rate of the carbonylation reaction, measured in step (a) is decreased, an amount of Lewis acid, or a precursor to the Lewis acid, that is proportional to the decrease in the rate of the carbonylation reaction is added to the carbonylation reaction vessel. In some embodiments, if the rate of the carbonylation reaction, measured in step (a) is decreased, an amount of the metal carbonyl or a precursor to the metal carbonyl, that is proportional to the decrease in the rate of the carbonylation reaction is added to the carbonylation reaction vessel. For example, if the rate of the carbonylation reaction has decreased by 5%, an amount of Lewis acid, precursor to the Lewis acid, metal carbonyl, or precursor to the metal carbonyl that is equivalent to about 5% of the amount of the Lewis acid or metal carbonyl initially charged into the carbonylation reaction vessel is added.

In some embodiments, if the concentration of the metal carbonyl, measured in step (a) is increased in the product stream downstream from the carbonylation reaction vessel, an amount of metal carbonyl, or a precursor to the metal carbonyl that is proportional to the increase in the amount of metal carbonyl measured in step (a) is added to the carbonylation reaction vessel. In some embodiments, if the concentration of the metal carbonyl measured in step (a) is decreased within the carbonylation reaction vessel, an amount of metal carbonyl, or a precursor to the metal carbonyl, that is proportional to the decrease in the amount of metal carbonyl measured in step (a) is added to the carbonylation reaction vessel. For example, if the concentration of the metal carbonyl has decreased by 5%, an amount of the metal carbonyl or precursor to the metal carbonyl that is equivalent to about 5% of the amount of the metal carbonyl initially charged into the carbonylation reaction vessel is added. In some embodiments, if the concentration of the metal carbonyl decomposition product measured in step (a) is increased within the carbonylation reaction vessel, an amount of metal carbonyl, or a precursor to the metal carbonyl, that is proportional to the increase in the amount of metal carbonyl decomposition product measured in step (a) is added to the carbonylation reaction vessel. For example, if the concentration of the metal carbonyl decomposition product has increased to 5% of the initial concentration of metal carbonyl initially charged into the carbonylation reaction vessel, then an amount of the metal carbonyl or precursor to the metal carbonyl that is equivalent to about 5% of the amount of the metal carbonyl initially charged is added.

II. Carbonylation Catalyst

As described generally above, carbonylation catalysts utilized in the processes described herein comprise a Lewis acid and a metal carbonyl. Typically, in one variation, a single metal carbonyl compound is provided, but in some embodiments, mixtures of two or more metal carbonyl compounds are provided. Thus, when a provided metal carbonyl compound "comprises", e.g., a neutral metal carbonyl compound, it is understood that the provided metal carbonyl compound can be a single neutral metal carbonyl compound, or a neutral metal carbonyl compound in combination with one or more metal carbonyl compounds. Preferably, the provided metal carbonyl compound is capable of ring-opening an epoxide and facilitating the insertion of CO into the resulting metal carbon bond. Metal carbonyl compounds with this reactivity are well known in the art and are used for laboratory experimentation as well as in industrial processes such as hydroformylation.

In some embodiments, the metal carbonyl compound comprises an anionic metal carbonyl moiety. In other embodiments, the metal carbonyl compound comprises a neutral metal carbonyl compound. In some embodiments, the metal carbonyl compound comprises a metal carbonyl hydride or a hydrido metal carbonyl compound. In some embodiments, the metal carbonyl compound acts as a pre-catalyst which reacts in situ with one or more reaction components to provide an active species different from the compound initially provided. Such pre-catalysts are specifically encompassed as it is recognized that the active species in a given reaction may not be known with certainty; thus the identification of such a reactive species in situ does not itself depart from the spirit or teachings herein.

In certain embodiments, the hydrido metal carbonyl (either as provided or generated in situ) comprises one or more of $HCo(CO)_4$, $HCoQ(CO)_3$, $HMn(CO)_5$, $HMn(CO)_4Q$, $HW(CO)_3Q$, $HRe(CO)_5$, $HMo(CO)_3Q$, $HOs(CO)_2Q$, $HMo(CO)_2Q_2$, $HFe(CO_2)Q$, $HW(CO)_2Q_2$, $HRuCOQ_2$, $H_2Fe(CO)_4$ or $H_2Ru(CO)_4$, where each Q is independently as defined above and in the classes and subclasses herein. In certain embodiments, the metal carbonyl hydride (either as provided or generated in situ) comprises $HCo(CO)_4$. In certain embodiments, the metal carbonyl hydride (either as provided or generated in situ) comprises $HCo(CO)_3PR_3$, where each R is independently an optionally substituted aryl group, an optionally substituted $C_{1-20}$ aliphatic group, an optionally substituted $C_{1-10}$ alkoxy group, or an optionally substituted phenoxy group. In certain embodiments, the metal carbonyl hydride (either as provided or generated in situ) comprises $HCo(CO)_3cp$, where cp represents an optionally substituted pentadienyl ligand. In certain embodiments, the metal carbonyl hydride (either as provided or generated in situ) comprises $HMn(CO)_5$. In certain embodiments, the metal carbonyl hydride (either as provided or generated in situ) comprises $H_2Fe(CO)_4$.

In some embodiments, the metal carbonyl compound comprises an anionic metal carbonyl species. In some embodiments, such anionic metal carbonyl species have the general formula $[Q_dM'_e(CO)_w]^{y-}$, where Q is any ligand and need not be present, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. In some embodiments, the anionic metal carbonyl has the general formula $[QM'(CO)_w]^{y-}$, where Q is any ligand and need not be present, M' is a metal atom, w is a number such as to provide the stable anionic metal carbonyl, and y is the charge of the anionic metal carbonyl.

In some embodiments, the anionic metal carbonyl species include monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, for example, $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, and $[Mn(CO)_5]^-$. In some embodiments, the anionic metal carbonyl comprises $[Co(CO)_4]^-$. In some embodiments, a mixture of two or more anionic metal carbonyl complexes may be present in the carbonylation catalysts used in the methods.

The term "such as to provide a stable anionic metal carbonyl" for $[Q_dM'_e(CO)_w]^{y-}$ is used herein to mean that $[Q_dM'_e(CO)_w]^{y-}$ is a species characterizable by analytical means, e.g., NMR, IR, X-ray crystallography, Raman spectroscopy and/or electron spin resonance (EPR) and isolable in catalyst form in the presence of a suitable cation or a species formed in situ. It is to be understood that metals which can form stable metal carbonyl complexes have known coordinative capacities and propensities to form polynuclear complexes which, together with the number and character of optional ligands Q that may be present and the charge on the complex will determine the number of sites available for CO to coordinate and therefore the value of w. Typically, such compounds conform to the "18-electron rule". Such knowledge is within the grasp of one having ordinary skill in the arts pertaining to the synthesis and characterization of metal carbonyl compounds.

In embodiments where the metal carbonyl compound is an anionic species, one or more cations must also necessarily be present. The present disclosure places no particular constraints on the identity of such cations. For example, in certain embodiments, the metal carbonyl anion is associated with a cationic Lewis acid. In other embodiments a cation associated with a provided anionic metal carbonyl compound is a simple metal cation such as those from Groups 1 or 2 of the periodic table (e.g. $Na^+$, $Li^+$, $K^+$, and $Mg^{2+}$). In other embodiments a cation associated with a provided anionic metal carbonyl compound is a bulky non electrophilic cation such as an 'onium salt' (e.g. $Bu_4N^+$, $PPM^+$, $Ph_4P^+$, and $Ph_4As^+$). In other embodiments, a metal carbonyl anion is associated with a protonated nitrogen compound (e.g., a cation may comprise a compound such as MeTBD-$H^+$, DMAP-$H^+$, DABCO-$H^+$, and DBU-$H^+$). In some embodiments, compounds comprising such protonated nitrogen compounds are provided as the reaction product between an acidic hydrido metal carbonyl compound and a basic nitrogen-containing compound (e.g., a mixture of DBU and $HCo(CO)_4$).

In certain embodiments, the metal carbonyl compound comprises a neutral metal carbonyl. In certain embodiments, such neutral metal carbonyl compounds have the general formula $Q_dM'e(CO)_{w'}$, where Q is any ligand and need not be present, M' is a metal atom, d is an integer between 0 and 8 inclusive, e is an integer between 1 and 6 inclusive, and w' is a number such as to provide the stable neutral metal carbonyl complex. In certain embodiments, the neutral metal carbonyl has the general formula $QM'(CO)_{w'}$. In certain embodiments, the neutral metal carbonyl has the general formula M'(CO)$_{w'}$. In certain embodiments, the neutral metal carbonyl has the general formula QM'$_2$(CO)$_{w'}$. In certain embodiments, the neutral metal carbonyl has the general formula M'$_2$(CO)$_{w'}$. Suitable neutral metal carbonyl compounds include, for example, Ti(CO)$_7$, V$_2$(CO)$_{12}$, Cr(CO)$_6$, Mo(CO)$_6$, W(CO)$_6$, Mn$_2$(CO)$_{10}$, Tc$_2$(CO)$_{10}$, Re$_2$(CO)$_{10}$, Fe(CO)$_5$, Ru(CO)$_5$, Os(CO)$_5$, Ru$_3$(CO)$_{12}$, Os$_3$(CO)$_{12}$Fe$_3$(CO)$_{12}$, Fe$_2$(CO)$_9$, Co$_4$(CO)$_{12}$, Rh$_4$(CO)$_{12}$, Rh$_6$(CO)$_{16}$, Ir$_4$(CO)$_{12}$, Co$_2$(CO)$_8$, and Ni(CO)$_4$.

The term "such as to provide a stable neutral metal carbonyl for Q$_d$M'$_e$(CO)$_{w'}$," is used herein to mean that Q$_d$M'$_e$(CO)$_{w'}$, is a species that may be characterized by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for CO to coordinate and therefore the value of w'. Typically, such compounds conform to stoichiometries conforming to the "18-electron rule". Such knowledge is within the grasp of one having ordinary skill in the arts pertaining to the synthesis and characterization of metal carbonyl compounds.

In some embodiments, no ligands Q are present on the metal carbonyl compound. In other embodiments, one or more ligands Q are present on the metal carbonyl compound. In some embodiments, where Q is present, each occurrence of Q is selected from the group consisting of phosphine ligands, amine ligands, cyclopentadienyl ligands, heterocyclic ligands, nitriles, phenols, and combinations of two or more of these. In some embodiments, one or more of the CO ligands of any of the metal carbonyl compounds described above is replaced with a ligand Q. In some embodiments, Q is a phosphine ligand. In some embodiments, Q is a triaryl phosphine. In some embodiments, Q is trialkyl phosphine. In some embodiments, Q is a phosphite ligand. In some embodiments, Q is an optionally substituted cyclopentadienyl ligand. In some embodiments, Q is cp. In some embodiments, Q is cp*. In some embodiments, Q is an amine or a heterocycle.

In certain embodiments, for any of the metal carbonyl compounds described above, M' comprises a transition metal. In certain embodiments, for any of the metal carbonyl compounds described above, M' is selected from Groups 5 (Ti) to 10 (Ni) of the periodic table. In certain embodiments, M' is a Group 9 metal. In certain embodiments, M' is Co. In certain embodiments, M' is Rh. In certain embodiments, M' is Ir. In certain embodiments, M' is Fe. In certain embodiments, M' is Mn.

As described generally above, carbonylation catalysts utilized in the processes described herein comprise a Lewis acid. In some embodiments, the carbonylation catalyst includes an anionic metal carbonyl complex and a cationic Lewis acidic component. In some embodiments, the metal carbonyl complex includes a carbonyl cobaltate and the Lewis acidic co-catalyst includes a metal-centered cationic Lewis acid. In some embodiments, an included Lewis acid comprises a boron compound.

In some embodiments, where an included Lewis acid comprises a boron compound, the boron compound comprises a trialkyl boron compound or a triaryl boron compound. In some embodiments, an included boron compound comprises one or more boron-halogen bonds. In some embodiments, where an included boron compound comprises one or more boron-halogen bonds, the compound is a dialkyl halo boron compound (e.g., R$_2$BX), a dihalo monoalkyl compound (e.g., RBX$_2$), an aryl halo boron compound (e.g., Ar$_2$BX or ArBX$_2$), or a trihalo boron compound (e.g., BCl$_3$ or BBr$_3$), wherein each R is an alkyl group; each X is a halogen; and each Ar is an aromatic group.

In some embodiments, where the included Lewis acid comprises a metal-centered cationic Lewis acid, the Lewis acid is a cationic metal complex. In some embodiments, the cationic metal complex has its charge balanced either in part, or wholly by one or more anionic metal carbonyl moieties. Suitable anionic metal carbonyl compounds include those described above. In some embodiments, there are 1 to 17 such anionic metal carbonyls balancing the charge of the cationic metal complex. In some embodiments, there are 1 to 9 such anionic metal carbonyls balancing the charge of the metal complex. In some embodiments, there are 1 to 5 such anionic metal carbonyls balancing the charge of the metal complex. In some embodiments, there are 1 to 3 such anionic metal carbonyls balancing the charge of the metal complex.

In some embodiments, where carbonylation catalysts used in methods described herein include a cationic metal complex, the metal complex has the formula [(L$^c$)$_v$M$_b$]$^{z+}$, where:

L$^c$ is a ligand where, when two or more L$^c$ are present, each may be the same or different;

M is a metal atom where, when two M are present, each may be the same or different;

v is an integer from 1 to 4 inclusive;

b is an integer from 1 to 2 inclusive; and z is an integer greater than 0 that represents the cationic charge on the metal complex.

In some embodiments, provided Lewis acids conform to structure I:

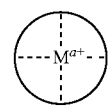

I wherein:

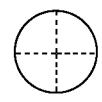

is a multidentate ligand;

M is a metal atom coordinated to the multidentate ligand;

a is the charge of the metal atom and ranges from 0 to 2; and

In some embodiments, provided metal complexes conform to structure II:

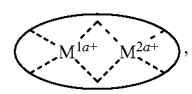

II where a is as defined above (each a may be the same or different), and

M$^1$ is a first metal atom;

$M^2$ is a second metal atom; and

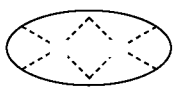

comprises a multidentate ligand system capable of coordinating both metal atoms.

For sake of clarity, and to avoid confusion between the net and total charge of the metal atoms in complexes I and II and other structures herein, the charge ($a^+$) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net charge of +1, and a would be 1.

Suitable multidentate ligands include, for example, porphyrin ligands 1, salen ligands 2, dibenzotetramethyltetraaza[14]annulene (tmtaa) ligands 3, phthalocyaninate ligands 4, the Trost ligand 5, tetraphenylporphyrin ligands 6, and corrole ligands 7. In some embodiments, the multidentate ligand is a salen ligand. In other embodiments, the multidentate ligand is a porphyrin ligand. In other embodiments, the multidentate ligand is a tetraphenylporphyrin ligand. In other embodiments, the multidentate ligand is a corrole ligand. Any of the foregoing ligands can be unsubstituted or can be substituted. Numerous variously substituted analogs of these ligands are known in the art and will be apparent to the skilled artisan.

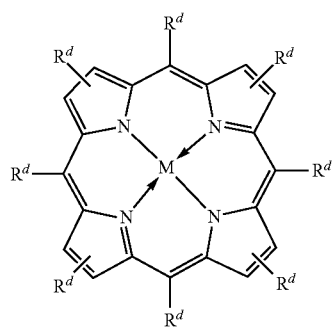

1

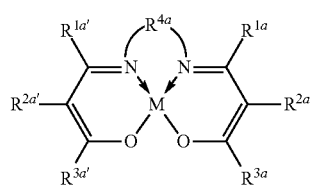

2

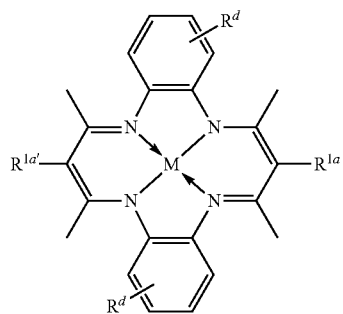

3

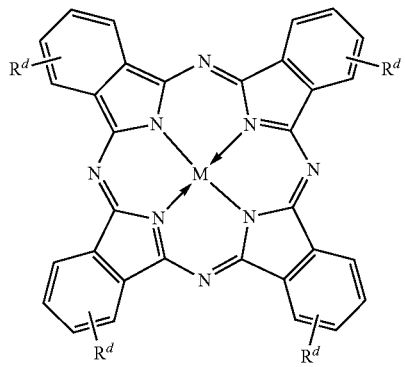

4

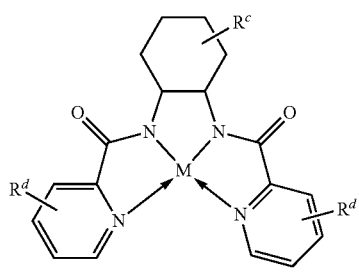

5

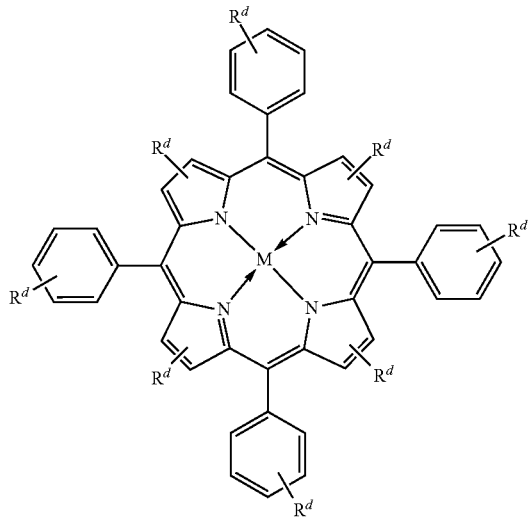

6

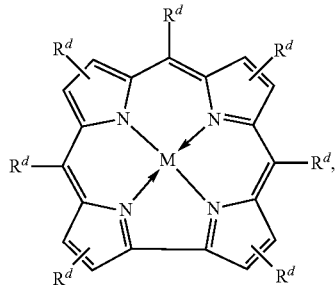

7 where each of $R^c$, $R^d$, $R^{1a}$, $R^{2a}$, $R^{3a}$, $R^{4a}$, $R^{1a'}$, $R^{2a'}$, $R^{3a'}$, and M, is as defined and described in the classes and subclasses herein.

In some embodiments, Lewis acids provided carbonylation catalysts used in methods described herein comprise metal-porphinato complexes. In some embodiments, the moiety

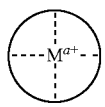

has the structure:

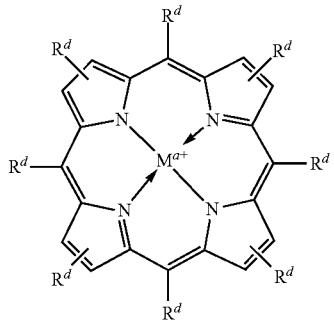

where each of M and a is as defined above and described in the classes and subclasses herein, and $R^d$ at each occurrence is independently hydrogen, halogen, $-OR^4$, $-NR^y_2$, $-SR^y$, $-CN$, $-NO_2$, $-SO_2R^y$, $-SOR^y$, $-SO_2NR^y_2$; $-CNO$, $-NR^ySO_2R^y$, $-NCO$, $-N_3$, $-SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur, where two or more $R^d$ groups may be taken together to form one or more optionally substituted rings;

each $R^y$ is independently hydrogen, an optionally substituted group selected the group consisting of acyl; carbamoyl, arylalkyl; 6- to 10-membered aryl; $C_{1-12}$ aliphatic; $C_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each $R^4$ is independently is a hydroxyl protecting group or $R^y$.

In some embodiments, the moiety

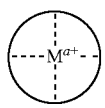

has the structure:

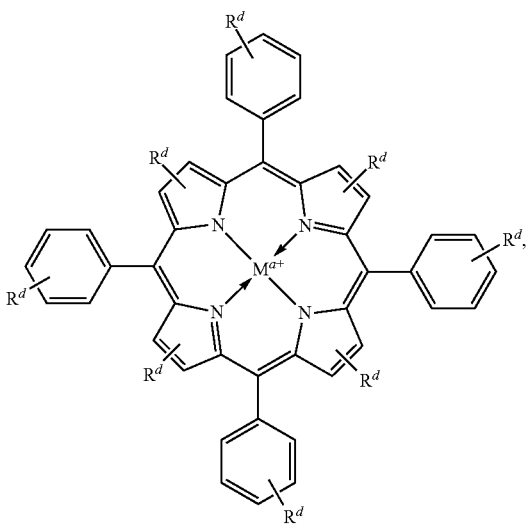

where M, a and $R^d$ are as defined above and in the classes and subclasses herein.

In some embodiments, the moiety

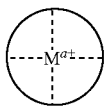

has the structure:

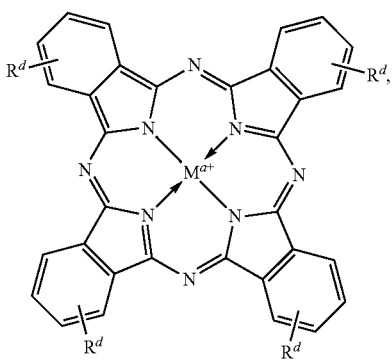

where M, a and $R^d$ are as defined above and in the classes and subclasses herein.

In some embodiments, Lewis acids included in carbonylation catalysts used in methods described herein comprise metallo salenate complexes. In some embodiments, the moiety

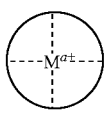

has the structure:

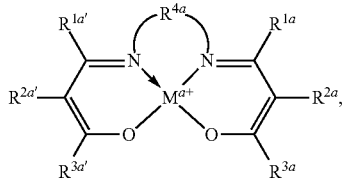

wherein:
M, and a are as defined above and in the classes and subclasses herein.
$R^{1a}$, $R^{1a'}$, $R^{2a}$, $R^{2a'}$, $R^{3a}$, and $R^{3a'}$ are independently hydrogen, halogen, —$OR^4$, —$NR^y{}_2$, —CN, —$NO_2$, —$SO_2R^y$, —$SOR^y$, —$SO_2NR^y{}_2$; —CNO, —$NR^ySO_2R^y$, —NCO, —$N_3$, —$SiR^y{}_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; wherein each $R^4$, and $R^y$ is independently as defined above and as described in classes and subclasses herein, wherein any of ($R^{2a'}$ and $R^{3a'}$), ($R^{2a}$ and $R^{3a}$), ($R^{1a}$ and $R^{2a}$), and ($R^{1a'}$ and $R^{2a'}$) may optionally be taken together with the carbon atoms to which they are attached to form one or more rings which may in turn be substituted with one or more $R^y$ groups; and
$R^{4a}$ is selected from the group consisting of:

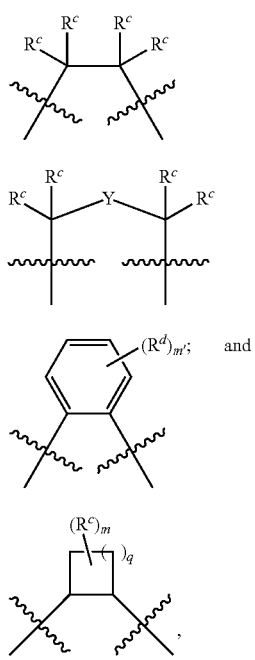

where
$R^c$ at each occurrence is independently hydrogen, halogen, —$OR^4$, —$NR^y{}_2$, —$SR^y$, —CN, —$NO_2$, —$SO_2R^y$, —$SOR^y$, —$SO_2NR^y{}_2$; —CNO, —$NR^ySO_2R^y$, —NCO, —$N_3$, —$SiR^y{}_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;

where:
two or more $R^c$ groups may be taken together with the carbon atoms to which they are attached and any intervening atoms to form one or more rings;
when two $R^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;
where $R^4$ and $R^y$ are as defined above and in classes and subclasses herein;
Y is a divalent linker selected from the group consisting of: —$NR^y$—, —$N(R^y)C(O)$—, —$C(O)NR^y$—, —O—, —C(O)—, —OC(O)—, —C(O)O—, —S—, —SO—, —$SO_2$—, —C(=S)—, —C(=$NR^y$)—, —N=N—; a polyether; a $C_3$ to $C_8$ substituted or unsubstituted carbocycle; and a $C_1$ to $C_8$ substituted or unsubstituted heterocycle;
m' is 0 or an integer from 1 to 4, inclusive;
q is 0 or an integer from 1 to 4, inclusive; and
x is 0, 1, or 2.
In some embodiments, a provided Lewis acid comprises a metallo salen compound, as shown in formula Ia:

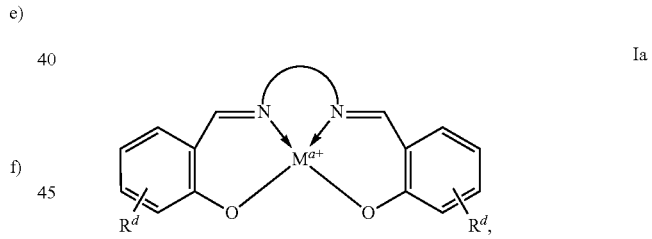

wherein each of M, $R^d$, and a, is as defined above and in the classes and subclasses herein,

represents is an optionally substituted moiety linking the two nitrogen atoms of the diamine portion of the salen ligand, where is selected from the group consisting of a $C_3$-$C_{14}$ carbocycle, a $C_6$-$C_{10}$ aryl group, a $C_3$-$C_{14}$ heterocycle, and a $C_5$-$C_{10}$ heteroaryl group; or an optionally substituted $C_{2-20}$ aliphatic group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)—, —C(O)O—, —S—, —SO—, —SO$_2$—, —C(=S)—, —C(=NR$^y$)—, —C(=NOR$^y$)— or —N=N—.
In some embodiments metal complexes having formula Ia above, at least one of the phenyl rings comprising the salicylaldehyde-derived portion of the metal complex is independently selected from the group consisting of:
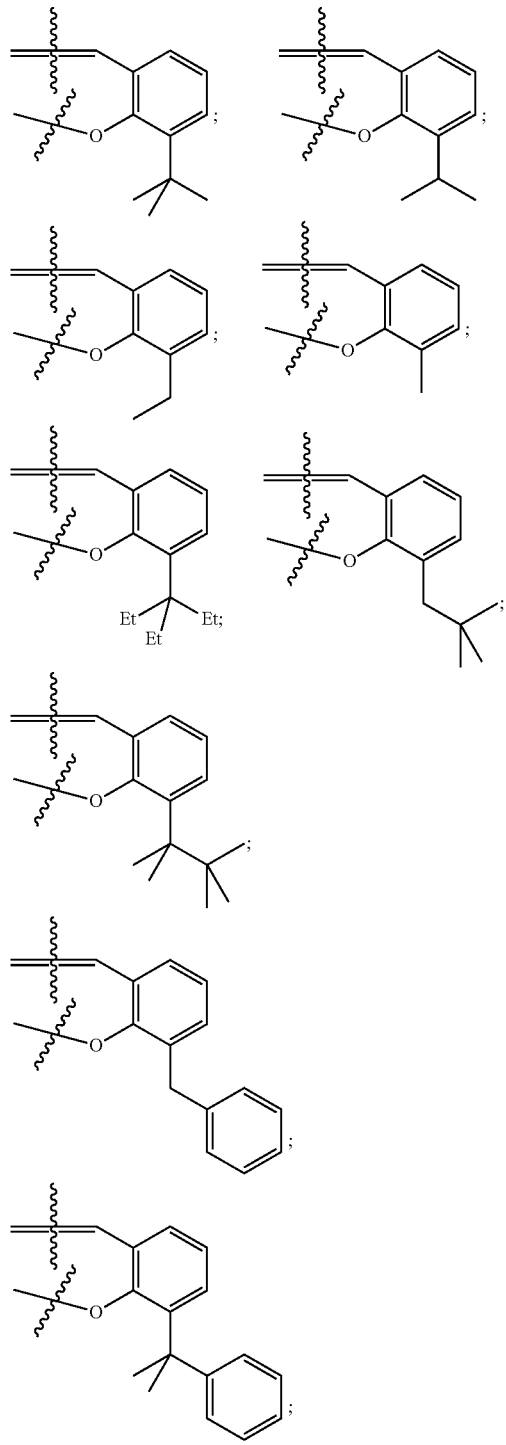
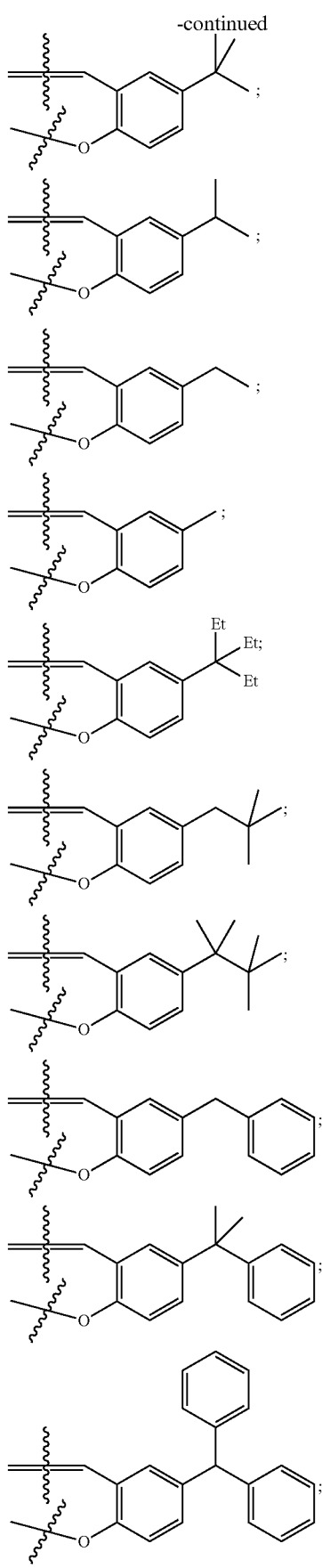

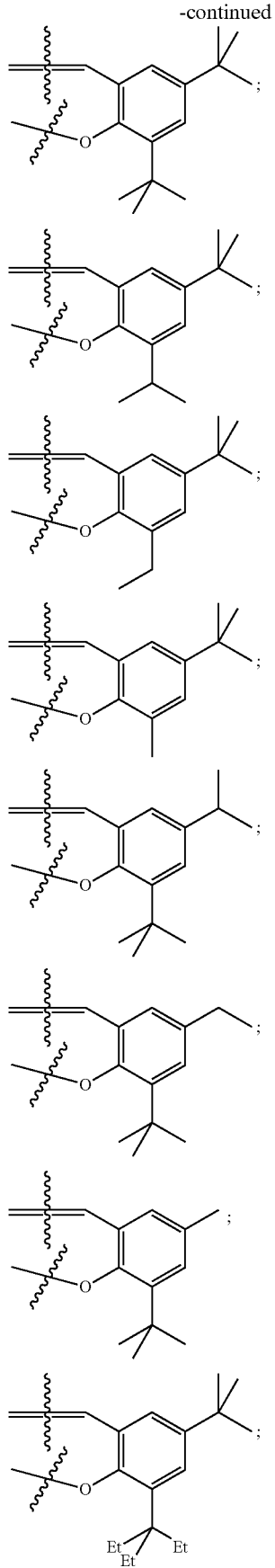
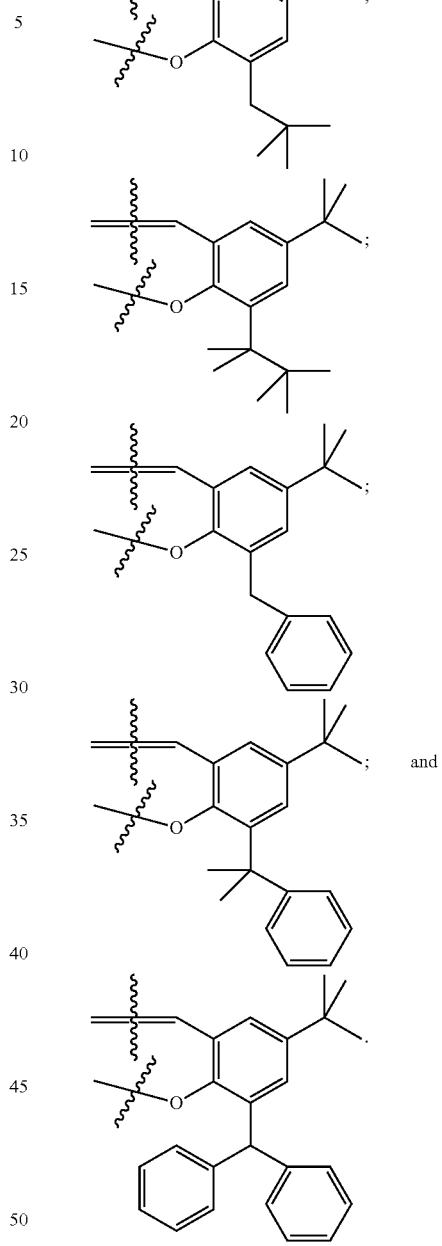
In some embodiments, a provided Lewis acid comprises a metallo salen compound, conforming to one of formulae Va or Vb:
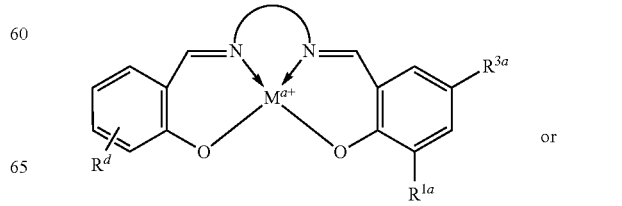

-continued

Vb where M, a, $R^d$, $R^{1a}$, $R^{3a}$, $R^{1a'}$, $R^{3a'}$, and are as defined above and in the classes and subclasses herein.

In some embodiments of metal complexes having formulae Va or Vb, each $R^{1a}$ and $R^{3a}$ is, independently, optionally substituted $C_1$-$C_{20}$ aliphatic.

In some embodiments, the moiety comprises an optionally substituted 1,2-phenyl moiety.

In some embodiments, Lewis acids included in carbonylation catalysts used in methods described herein comprise metal-tmtaa complexes. In some embodiments, the moiety has the structure:

where M, a and $R^d$ are as defined above and in the classes and subclasses herein, and $R^e$ at each occurrence is independently hydrogen, halogen, —OR, —NR$^y$$_2$, —SR$^y$, —CN, —NO$_2$, —SO$_2$R$^y$, —SOR$^y$, —SO$_2$NR$^y$$_2$; —CNO, —NR$^y$SO$_2$R$^y$, —NCO, —N$_3$, —SiR$^y$$_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur.

In some embodiments, the moiety has the structure:

where each of M, a, $R^c$ and $R^d$ is as defined above and in the classes and subclasses herein.

In some embodiments, where carbonylation catalysts used in methods described herein include a Lewis acidic metal complex, the metal atom is selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium.

In some embodiments, M has an oxidation state of +2. In some embodiments, M is Zn(II), Cu(II), Mn(II), Co(II), Ru(II), Fe(II), Co(II), Rh(II), Ni(II), Pd(II) or Mg(II). In some embodiments M is Zn(II). In some embodiments M is Cu(II).

In some embodiments, M has an oxidation state of +3. In some embodiments, M is Al(III), Cr(III), Fe(III), Co(III), Ti(III) In(III), Ga(III) or Mn(III). In some embodiments M is Al(III). In some embodiments M is Cr(III).

In some embodiments, M has an oxidation state of +4. In some embodiments, M is Ti(IV) or Cr(IV).

In some embodiments, $M^1$ and $M^2$ are each independently a metal atom selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium. In some embodiments, $M^1$ and $M^2$ are the same. In some embodiments, $M^1$ and $M^2$ are the same metal, but have different oxidation states. In some embodiments, $M^1$ and $M^2$ are different metals.

In some embodiments, one or more of $M^1$ and $M^2$ has an oxidation state of +2. In some embodiments, $M^1$ is Zn(II), Cu(II), Mn(II), Co(II), Ru(II), Fe(II), Co(II), Rh(II), Ni(II), Pd(II) or Mg(II). In some embodiments $M^1$ is Zn(II). In some embodiments $M^1$ is Cu(II). In some embodiments, $M^2$ is Zn(II), Cu(II), Mn(II), Co(II), Ru(II), Fe(II), Co(II), Rh(II), Ni(II), Pd(II) or Mg(II). In some embodiments $M^2$ is Zn(II). In some embodiments $M^2$ is Cu(II).

In some embodiments, one or more of $M^1$ and $M^2$ has an oxidation state of +3. In some embodiments, $M^1$ is Al(III), Cr(III), Fe(III), Co(III), Ti(III) In(III), Ga(III) or Mn(III). In some embodiments $M^1$ is Al(III). In some embodiments $M^1$ is Cr(III). In some embodiments, $M^2$ is Al(III), Cr(III), Fe(III), Co(III), Ti(III) In(III), Ga(III) or Mn(III). In some embodiments $M^2$ is Al(III). In some embodiments $M^2$ is Cr(III).

In some embodiments, one or more of $M^1$ and $M^2$ has an oxidation state of +4. In some embodiments, $M^1$ is Ti(IV) or Cr(IV). In some embodiments, $M^2$ is Ti(IV) or Cr(IV).

In some embodiments, the metal-centered Lewis-acidic component of the carbonylation catalyst includes a dianionic tetradentate ligand. In some embodiments, the dianionic tetradentate ligand is selected from the group consisting of: porphyrin ligands; salen ligands; dibenzotetramethyltetraaza[14]annulene (tmtaa) ligands; phthalocyaninate ligands; and the Trost ligand.

In some embodiments, the carbonylation catalyst includes a carbonyl cobaltate in combination with an aluminum porphyrin compound. In some embodiments, the carbonylation catalyst is $[(TPP)Al(THF)_2][Co(CO)_4]$ where TPP stands for tetraphenylporphyrin and THF stands for tetrahydrofuran.

In some embodiments, the carbonylation catalyst includes a carbonyl cobaltate in combination with a chromium porphyrin compound.

In some embodiments, the carbonylation catalyst includes a carbonyl cobaltate in combination with a chromium salen compound. In some embodiments, the carbonylation catalyst includes a carbonyl cobaltate in combination with a chromium salophen compound.

In some embodiments, the carbonylation catalyst includes a carbonyl cobaltate in combination with an aluminum salen compound. In some embodiments, the carbonylation catalyst includes a carbonyl cobaltate in combination with an aluminum salophen compound.

In some embodiments, one or more neutral two electron donors coordinate to M, $M^1$ or $M^2$ and fill the coordination valence of the metal atom. In some embodiments, the neutral two electron donor is a solvent molecule. In some embodiments, the neutral two electron donor is an ether. In some embodiments, the neutral two electron donor is tetrahydrofuran, diethyl ether, acetonitrile, carbon disulfide, or pyridine. In some embodiments, the neutral two electron donor is tetrahydrofuran. In some embodiments, the neutral two electron donor is an epoxide. In some embodiments, the neutral two electron donor is an ester or a lactone.

III. Catalyst Replacement Components

As described generally above, each of the one or more catalyst replacement components described herein comprise species independently selected from the group consisting of the Lewis acid, a precursor to the Lewis acid, the metal carbonyl, or a precursor to the metal carbonyl. In some embodiments one of the one or more catalyst replacement components comprises the Lewis acid. In some embodiments one of the one or more catalyst replacement components comprises a precursor to the Lewis acid. In some embodiments one of the one or more catalyst replacement components comprises the metal carbonyl. In some embodiments one of the one or more catalyst replacement components comprises a precursor to the metal carbonyl.

In certain embodiments, the Lewis acid used as a catalyst replacement component is selected from the Lewis acids described in classes and subclasses above in Section II describing the catalysts. One of skill in the art will appreciate that where a given Lewis acid is ionized, it is accompanied by a counterion. Where the catalyst is an ionic pair of a charged Lewis acid and a charged metal carbonyl, if only the Lewis acid is to be added as a catalyst replacement component, then it must be added together with a counterion to be substituted by the charged metal carbonyl once inside the carbonylation reaction vessel.

The addition of the Lewis acid (either as a neutral or ionic species) is distinguished from the addition of a Lewis acid precursor. The term "Lewis acid precursor", as used herein is defined as a species, other than a Lewis acid or salt thereof, that when added to the carbonylation reaction vessel, regenerates the Lewis acid species when contacted by one or more other components within the carbonylation reaction vessel. Lewis acid precursors may include, for example, multidentate ligands and multidentate ligand systems (with or without coordinated metal atoms), neutral two-electron donors, and labile metal sources such as metals including a carbon-metal bond. Suitable multidentate ligands and neutral two-electron donors are described in Section II describing the catalysts, and described herein in classes and subclasses. Suitable labile metal sources include, for example, alkyl metals (e.g., trialkylaluminums, and trialkylchromiums), or aryl metals (e.g., triarylaluminums, and triarylchromiums).

In some embodiments, a Lewis acid precursor includes a multidentate ligand of one of the following formulas:

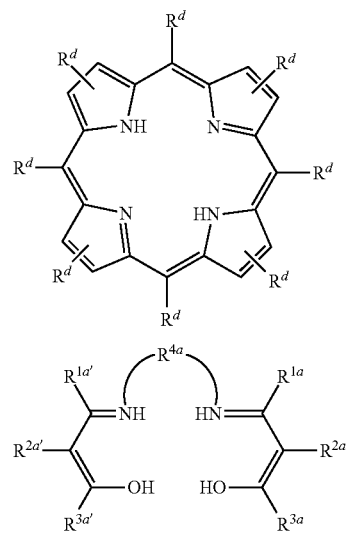

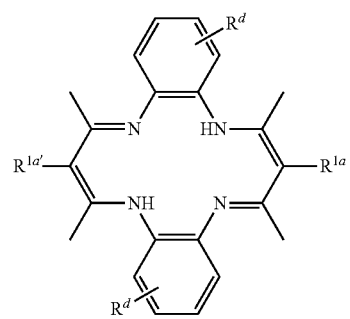

-continued

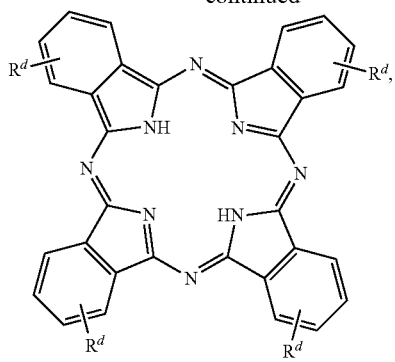

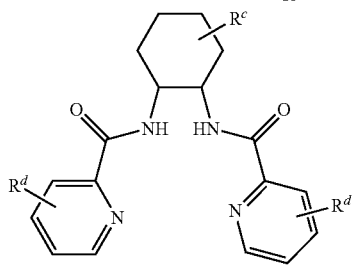

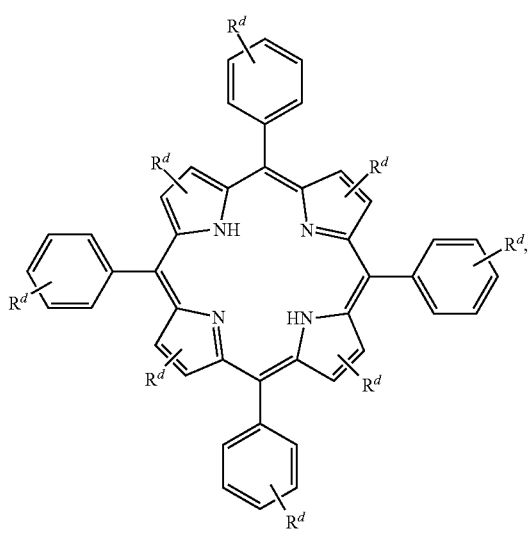

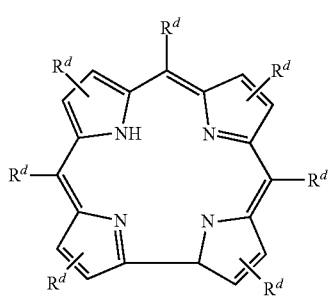

where each of $R^c$, $R^d$, $R^{1a}$, $R^{2a}$, $R^{3a}$, $R^{4a}$, $R^{1a'}$, $R^{2a'}$, and $R^{3a'}$, is as defined and described in the classes and subclasses herein.

In some embodiments, Lewis acid precursors have the following formula:

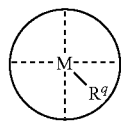

wherein:

is a multidentate ligand;
M is a metal atom coordinated to the multidentate ligand; and
$R^q$ is selected from $C_{1-12}$ aliphatic and optionally substituted aryl.

In some embodiments, Lewis acid precursors have the following formula:

wherein:
$M^1$ is a first metal atom;
$M^2$ is a second metal atom;

comprises a multidentate ligand system capable of coordinating both metal atoms; and
each $R^q$ is independently selected from $C_{1-12}$ aliphatic and optionally substituted aryl.

In some embodiments, $R^q$ is $C_{1-6}$ aliphatic. In some embodiments, $R^q$ is methyl. In some embodiments, $R^q$ is ethyl. In some embodiments, $R^q$ is optionally substituted aryl. In some embodiments, $R^q$ is optionally substituted phenyl. In some embodiments, $R^q$ is phenyl.

In certain embodiments, the metal carbonyl used as a catalyst replacement component is selected from the metal carbonyls described in classes and subclasses above in Section II ("Catalysts"). One of skill in the art will appreciate that where a given metal carbonyl is ionized, it is accompanied by a counterion. Where the catalyst is an ionic pair of a charged Lewis acid and a charged metal carbonyl, if only the metal carbonyl is to be added as a catalyst replacement component, then it must be added together with a counterion which will subsequently be substituted by the charged Lewis acid in situ.

The addition of the metal carbonyl (either as a neutral or ionic species) is distinguished from the addition of a metal carbonyl precursor. The term "metal carbonyl precursor", as used herein is defined as a species that, when added to the carbonylation reaction vessel, regenerates the metal carbonyl species when contacted by one or more other components within the carbonylation reaction vessel. Examples of metal carbonyl precursors include, for example, neutral metal carbonyl compounds.

In some embodiments, such neutral metal carbonyl compounds have the general formula $Q_dM'_e(CO)_{w'}$, where Q is any ligand and need not be present, M' is a metal atom, d is an integer between 0 and 8 inclusive, e is an integer between 1 and 6 inclusive, and w' is a number such as to provide the stable neutral metal carbonyl complex. In some embodiments, the neutral metal carbonyl has the general formula $QM'(CO)_{w'}$. In some embodiments, the neutral metal carbonyl has the general formula $M'_2(CO)_{w'}$. In some embodiments, the neutral metal carbonyl has the general formula $QM'_2(CO)_{w'}$. In some embodiments, the neutral metal carbonyl has the general formula $M'_2(CO)_{w'}$. Suitable neutral metal carbonyl compounds include, for example, $Ti(CO)_7$; $V_2(CO)_{12}$; $Cr(CO)_6$; $Mo(CO)_6$; $W(CO)_6$; $Mn_2(CO)_{10}$; $Tc_2(CO)_{10}$; $Re_2(CO)_{10}$; $Fe(CO)_5$; $Ru(CO)_5$; $Os(CO)_5$; $Ru_3(CO)_{12}$; $Os_3(CO)_{12}$; $Fe_3(CO)_{12}$; $Fe_2(CO)_9$; $Co_4(CO)_{12}$; $Rh_4(CO)_{12}$; $Rh_6(CO)_{16}$; $Ir_4(CO)_{12}$; $Co_2(CO)_8$; and $Ni(CO)_4$. In some embodiments, the metal carbonyl precursor is $Co_4(CO)_{12}$ or $Co_2(CO)_8$. In some embodiments, the metal carbonyl precursor is $Co_2(CO)_8$. In some embodiments, the metal carbonyl precursor is $Co_4(CO)_{12}$. In certain embodiments, the metal carbonyl precursor is a mixture of two or more cobalt carbonyl species.

In some embodiments, if the Lewis acid or metal carbonyl used as catalyst replacement components are added in ionic form, their counterions are selected to minimize contamination with halide and/or alkali metal ions. In certain embodiments, the catalyst replacement components are essentially free of halide. In certain embodiments, the catalyst replacement components have a halide content less than about 200 ppm. In certain embodiments, the catalyst replacement components have a halide content less than about 150 ppm, less than about 100 ppm, less than about 50 ppm, less than about 40 ppm, less than about 30 ppm, less than about 20 ppm, less than about 10 ppm, less than about 5 ppm, less than about 2 ppm, or less than about 1 ppm. In certain embodiments, the catalyst replacement components are essentially free of alkali metal ions. In certain embodiments, the catalyst replacement components have an alkali metal ion content less than about 200 ppm. In certain embodiments, the catalyst replacement components have an alkali metal ion content less than about 150 ppm, less than about 100 ppm, less than about 50 ppm, less than about 40 ppm, less than about 30 ppm, less than about 20 ppm, less than about 10 ppm, less than about 5 ppm, less than about 2 ppm, or less than about 1 ppm.

In some embodiments, a given catalyst replacement component is recycled from the product stream.

IV. Processes for Replacement of Catalyst Component at Predetermined Rate

In another aspect, provided is a process for continuous carbonylation of an epoxide or lactone feedstock, the process comprising:

reacting an epoxide or lactone feedstock with carbon monoxide in the presence of a catalyst comprising a Lewis acid and a metal carbonyl in a carbonylation reaction vessel; and continuously or intermittently introducing to the carbonylation reaction vessel a catalyst replacement component which is different from the catalyst and comprises a species selected from the group consisting of the Lewis acid, a precursor to the Lewis acid, the metal carbonyl, and a precursor to the metal carbonyl.

In some embodiments, the catalyst replacement component comprises the Lewis acid. In some embodiments, the catalyst replacement component comprises a precursor to the Lewis acid. In some embodiments, the catalyst replacement component comprises the metal carbonyl. In some embodiments, the catalyst replacement component comprises a precursor to the metal carbonyl.

Suitable catalyst replacement components (e.g., Lewis acids, precursors to Lewis acids, metal carbonyls, and precursors to metal carbonyls) are described in Section III above.

In some embodiments, the catalyst replacement component is introduced at a rate that results in less than 10% variation in the rate of the carbonylation reaction over a period of one hour. In some embodiments, the catalyst replacement component is introduced at a rate that results in less than 5% variation in the rate of the carbonylation reaction over a period of one hour.

In some embodiments, the rate at which the catalyst replacement component is added to the carbonylation reaction vessel is determined by the rate at which the carbonylation reaction rate has been observed to decrease. In some embodiments, the rate at which the one or more catalyst replacement components are added to the carbonylation reaction vessel is directly proportional to the rate at which the carbonylation reaction rate has been observed to decrease.

In some embodiments, the one or more catalyst replacement components are introduced continuously to the carbonylation reaction vessel at the same rate that the carbonylation reaction rate is observed to decrease. In some embodiments, the one or more catalyst replacement components are introduced intermittently to the carbonylation reaction vessel to produce an average rate which matches the rate at which the which the carbonylation reaction rate has been observed to decrease.

Thus if the carbonylation reaction rate has been observed to decrease 5% over the course of a time period, the catalyst replacement component may either be added continuously or intermittently at such a rate that 5% of the initial amount of Lewis acid or metal carbonyl present in the carbonylation reaction vessel is added over that same time period. In some embodiments, the catalyst replacement component is added continuously. In some embodiments, the catalyst replacement component is added every hour. In some embodiments, the catalyst replacement component is added every 30 minutes. In some embodiments, the catalyst replacement component is added every 15 minutes. In some embodiments, the catalyst replacement component is added every 10 minutes. In some embodiments, the catalyst replacement component is added every 5 minutes. In some embodiments, the catalyst replacement component is added every minute.

One of skill in the art will appreciate that the shorter the intervals at which the one or more catalyst replacement components are added, the less variation in the overall carbonylation reaction rate will be observed. However this must be balanced against other considerations such as the complexity of making multiple additions and the effects of noise in data generated by the measurements used to determine the addition rate.

V. Carbonylation Reaction Vessel and Catalyst Replacement Component Feed Streams The methods herein place no particular limits on the type, size or geometry of the reactor employed and indeed, in some cases, more than one reactor may be employed. It is to be understood that the term "reactor" as recited in the methods herein may actually represent more than one physical reactor (for example the reactor could be a train of continuous stirred tank reactors (CSTRs) connected in parallel or in series, or a plurality of plug flow reactors). In some embodiments, the "reactor" referred to in the methods herein may also comprise more than one type of reactor (for example the reactor could comprise a CSTR in series with a plug flow reactor).

Additional Processing Steps

In some embodiments, methods described herein comprise additional steps to isolate the carbonylation product from the reaction product stream. These steps typically entail further treatment of the product stream from which the catalyst or catalyst component has been substantially removed.

Thus, in some variations, the reacting of the epoxide or lactone feedstock with the carbon monoxide in the presence of the carbonylation catalyst in the carbonylation reaction vessel produces carbonylation products in a carbonylation product stream, and the methods described herein further comprises separating the carbonylation product stream from the carbonylation reaction vessel. For example, the carbonylation product stream may be separated from the carbonylation reaction vessel by a nanofiltration membrane. The nanofiltration membrane may retain at least a portion of the Lewis acid and the metal carbonyl, and permeates the carbonylation products. In some variations, the nanofiltration membrane is configured to retain solutes having a molecular weight greater than the molecular weight of the epoxide or lactone carbonylation products, and to allow solutes having lower molecular weights to permeate.

The precise mode of carrying out the carbonylation product isolation may depend on the character of the carbonylation product. Suitable isolation methods may include, for example, distillation, crystallization, precipitation, and evaporation. In embodiments where the carbonylation product is a liquid such as betapropiolactone or betabutyrolactone, the methods may further comprise performing distillation to separate the lactone from other components of the reaction product stream. Such other components can include, for example, solvent(s), unreacted epoxide, reaction byproducts, and catalyst residues. In embodiments where the solvent has a lower boiling point than the lactone, or where unreacted epoxide is present, the beta lactone may be retained as the bottoms in the distillation with the solvent and/or epoxide taken to the vapor phase. In embodiments where the solvent has a boiling point higher than the lactone and/or where non volatile catalyst residues are present, the lactone may be taken to the vapor phase. In some embodiments, the catalyst and/or unreacted epoxide are captured and fed back to the epoxide carbonylation reactor (either in real time, or via accumulation and use at a later time).

In embodiments where the carbonylation product is a solid such as succinic anhydride or polypropiolactone, the methods may further comprise crystallization or precipitation to separate the carbonylation product from other components of the reaction product stream. Such other components can include, for example, solvent(s), unreacted epoxide, reaction byproducts, and catalyst residues. In some embodiments, such methods include lowering the temperature of the reaction product stream. In some embodiments, such methods include removing solvent, excess epoxide and/or unreacted CO from the reaction product stream. In some embodiments, such methods comprise adding a solvent to the reaction product stream to cause precipitation or crystallization of the carbonylation product.

In some embodiments, the methods described above may include additional steps intermediate between the carbonylation reaction and catalyst separation. In some embodiments, such steps include reduction of the CO pressure. In some embodiments, the CO pressure is reduced to atmospheric pressure. In some embodiments, excess CO is removed by exposure to sub-atmospheric pressures or by sweeping with another gas. In some embodiments, the CO thus liberated is captured for re-use or is incinerated to provide heat. In some embodiments, the methods comprise heating or cooling the reaction product stream between the carbonylation reaction and catalyst separation. When methods include separation of a solid carbonylation product, they may include additional substeps such as filtration, washing and collection of the solid product.

In certain embodiments, the carbonylation reaction vessel comprises one or more continuous stirred tank reactors (CSTRs). In certain embodiments, the carbonylation reaction vessel comprises one or more plug flow reactors. In certain embodiments, the carbonylation reaction vessel is also fed with an epoxide feed stream and carbon monoxide. As used herein a catalyst replacement component being "added to the carbonylation reaction vessel" contemplates any situation in which a catalyst replacement component is introduced to the carbonylation reaction vessel, including directly adding it to the carbonylation reaction vessel, or adding it at any point in the process before that. In some embodiments, a given catalyst replacement component is added upstream from the carbonylation reaction vessel. In some embodiments, a given catalyst replacement component is added directly to the carbonylation reaction vessel. In some embodiments, a given catalyst replacement component is added to a feed stream of the reaction vessel (e.g. to the epoxide or carbon monoxide feed streams).

In certain embodiments where the one or more catalyst replacement components are added to a carbonylation reaction vessel, the reaction vessel is also fed with an epoxide feed stream and carbon monoxide. In some embodiments, a catalyst replacement component is added to the epoxide feed stream. In some embodiments, there is more than one epoxide feed stream. In some embodiments, a catalyst replacement component is added to at least one of the more than one epoxide feed streams. In some embodiments, a catalyst replacement component is added to one of the more than one epoxide feed streams, and one of the more than one epoxide feed streams does not contain added catalyst replacement component.

In some such embodiments, each catalyst replacement component is introduced to the reaction vessel in its own catalyst feed stream. The introduction of more than one catalyst replacement component, each in its own catalyst feed stream, is advantageous in a number of situations. One such situation is where the initial loading of the catalyst is formed in situ in the carbonylation reaction vessel from two catalyst precursors. Rather than remove the catalyst feed streams after the initial loading, those feed streams remain connected and are used to supplement the carbonylation reaction vessel with catalyst replacement components. In some embodiments, the depletion of each component of the two-component catalyst does not occur at the same rate. Accordingly, in some embodiments, each catalyst replacement component should be added at different times or at different rates, and multiple catalyst feed streams are helpful for accomplishing this. In other embodiments, individual catalyst replacement components may not have compatible physical or chemical properties, and it is necessary to keep them separate until they reach the carbonylation reaction vessel.

In some embodiments, a first catalyst replacement component is added to the carbonylation reaction vessel in a first catalyst feed stream and a second catalyst replacement component is added to the carbonylation reaction vessel in a second catalyst feed stream. In some embodiments the first catalyst feed stream and the second catalyst feed stream are fed to the carbonylation reaction vessel at rates such that a molar ratio of epoxide to catalyst replacement component fed to the continuous reactor per unit time is between about 10 and about 200,000 moles of epoxide per mole of the most rapidly added catalyst replacement component. In certain embodiments, the molar ratio of epoxide to most rapidly added catalyst replacement component fed to the reactor per unit time is between about 50 and about 50,000, between about 100 and about 20,000, between about 100 and about 10,000, between about 100 and about 5,000, or between about 100 and about 2,500. In certain embodiments, the molar ratio of epoxide to catalyst replacement component fed to the reactor per unit time is between about 100 and about 50,000, between about 100 and about 20,000, between about 100 and about 10,000, between about 100 and about 5,000, or between about 100 and about 2,500. In certain embodiments, the molar ratio of epoxide to catalyst replacement component fed to the reactor per unit time is between about 200 and about 20,000, between about 500 and about 10,000, between about 500 and about 5,000, between about 1,000 and about 5,000, between about 2,000 and about 5,000 between about 2,000 and about 3,000, or between about 5,000 and about 10,000. In certain embodiments, the molar ratio of epoxide to catalyst replacement component fed to the reactor per unit time is between about 50,000 and about 200,000, between about 50,000 and about 150,000, between about 50,000 and about 100,000, between about 100,000 and about 200,000, between about 100,000 and about 150,000, or between about 150,000 and about 200,000.

In certain embodiments, each of the catalyst replacement component feedstreams comprises solvent. In certain embodiments, such feed streams comprise an organic solvent selected from the group consisting of: aliphatic hydrocarbons, aromatic hydrocarbons, halogenated solvents, ethers, esters, ketones, nitriles, amides, carbonates, alcohols, amines, sulfones, or mixtures of any two or more of these. In certain embodiments, such feed streams comprise one or more ethers. In certain embodiments, an ether is selected from diethyl ether, methy-t-butyl ether, tetrahydrofuran, 1,4-dioxane, glyme, diglyme, triglyme, higher glymes, or mixtures of any two or more of these. In certain embodiments, such feed streams comprise 1,4-dioxane.

In certain embodiments, the first catalyst feed stream comprises a homogenous solution of a Lewis acid or precursor to the Lewis acid in an organic solvent. In certain embodiments, the first catalyst feed stream comprises a slurry of a Lewis acid or a precursor to the Lewis acid in an organic solvent. In certain embodiments, the first catalyst feed stream comprises a neutral two-electron donor. In some embodiments, the first catalyst feed stream comprises an ether. In some embodiments, the first catalyst feed stream comprises tetrahydrofuran. In certain embodiments, the first catalyst feed stream comprises 1,4-dioxane.

In certain embodiments, the second catalyst feed stream comprises a homogenous solution of a neutral metal carbonyl compound in an organic solvent. In certain embodiments, the second catalyst feed stream comprises a slurry of a neutral metal carbonyl compound in an organic solvent. In certain embodiments, the second catalyst feed stream comprises an ether. In certain embodiments, the second catalyst feed stream comprises tetrahydrofuran. In certain embodiments, the second catalyst feed stream comprises 1,4-dioxane.

In certain embodiments where at least one of the first or second carbonylation catalyst feed streams comprises an organic solvent, and where the epoxide carbonylation reaction is a continuous carbonylation process, the method is characterized in that there are no additional solvent feeds to the continuous reactor. Or put another way, the method is characterized in that all of the reaction solvent fed to the continuous epoxide carbonylation reaction is provided via the catalyst feed streams.

As mentioned above, one advantage of methods described herein is the ability to regenerate epoxide carbonylation catalysts that are essentially free of halide and/or alkali metal salt impurities. Therefore, in certain embodiments, provided are methods for feeding the carbonylation reaction vessel of an epoxide carbonylation reaction with one or more catalyst replacement components characterized in that the epoxide carbonylation reaction vessel remains essentially free of halide and/or alkali metal salt impurities introduced with the catalyst replacement components. In certain embodiments, where a catalyst replacement component is introduced in the form of a salt, said salt is not a halide or alkali metal salt. In certain embodiments, such methods are characterized in that the epoxide carbonylation reaction vessel is essentially free of halide. In certain embodiments, the methods are characterized in that the epoxide carbonylation reaction vessel has a halide content less than about 200 ppm. In certain embodiments, the methods are characterized in that the epoxide carbonylation reaction vessel has a halide content less than about 150 ppm, less than about 100 ppm, less than about 50 ppm, less than about 40 ppm, less than about 30 ppm, less than about 20 ppm, less than about 10 ppm, less than about 5 ppm, less than about 2 ppm, or less than about 1 ppm. In certain embodiments, the methods are characterized in that the epoxide carbonylation reaction vessel is essentially free of alkali metal salts. In certain embodiments, the methods are characterized in that the epoxide carbonylation reaction vessel has an alkali metal salt content less than about 200 ppm. In certain embodiments, the methods are characterized in that the epoxide carbonylation reaction vessel has an alkali metal salt content less than about 150 ppm, less than about 100 ppm, less than about 50 ppm, less than about 40 ppm, less than about 30 ppm, less than about 20 ppm, less than about 10 ppm, less than about 5 ppm, less than about 2 ppm, or less than about 1 ppm.

In certain embodiments of methods for providing catalyst replacement components to an epoxide carbonylation reaction, the neutral metal carbonyl compound provided in the second catalyst feed stream has the general formula $Q'_d M_e (CO)_{w'}$, where each of $Q'$, $M'$, d, e, and w' is as defined above and in the classes and subclasses herein. In certain embodiments, the neutral metal carbonyl provided in the second catalyst feed stream has the general formula $Q'M(CO)_{w'}$. In certain embodiments, the neutral metal carbonyl provided in the second catalyst feed stream has the general formula $M(CO)_{w'}$. In certain embodiments, the neutral metal carbonyl provided in the second catalyst feed stream has the general formula $Q'M_2(CO)_{w'}$. In certain embodiments, the neutral metal carbonyl provided in the second catalyst feed stream has the general formula $M_2(CO)_{w'}$. Suitable neutral metal carbonyl compounds include, for example, $(CO)_7$; $V_2(CO)_{12}$; $Cr(CO)_6$; $Mo(CO)_6$; $W(CO)_6 Mn_2(CO)_{10}$; $Tc_2(CO)_{10}$; $Re_2(CO)_{10}$; $Fe(CO)_5$; $Ru(CO)_5$; $Os(CO)_5$; $Ru_3(CO)_{12}$; $Os_3(CO)_{12}$; $Fe_3(CO)_{12}$; $Fe_2(CO)_9$; $Co_4(CO)_{12}$; $Rh_4(CO)_{12}$; $Rh_6(CO)_{16}$; $Ir_4(CO)_{12}$; $Co_2(CO)_8$; and $Ni(CO)_4$.

In certain embodiments, the neutral metal carbonyl compound provided in the second catalyst feed stream comprises a cobalt carbonyl compound. In certain embodiments, the neutral metal carbonyl compound provided in the second catalyst feed stream is $Co_2(CO)_8$. In certain embodiments, the neutral metal carbonyl compound provided in the second catalyst feed stream is $Co_4(CO)_{12}$. In certain embodiments, the neutral metal carbonyl compound provided in the second catalyst feed stream is a mixture of two or more cobalt carbonyl species.

In certain embodiments, the rate of addition of the first catalyst feed stream comprising the Lewis acid, or a precursor to the Lewis acid, and the rate of addition of the second catalyst feed stream, comprising the metal carbonyl or a precursor to the metal carbonyl, are set such that within the carbonylation reaction vessel, the molar ratio of metal carbonyl, to Lewis acid is maintained at a ratio of about 1:1.

It should generally be understood that reference to "a first feed stream" and "a second feed stream", etc., or "a first component" and "a second components", etc., does not necessarily imply an order of the feed streams or components. In some variations, the use of such references denotes the number of feed streams or components present. In other variations, an order may be implied by the context in which the feed streams or components are configured or used.

Carbonylation Reactions

Epoxide

In some variations, the methods herein involve the continuous carbonylation of epoxides. The catalytic insertion of CO into epoxides is known to yield several possible products the identity of which is influenced by the particular catalyst utilized and the reaction conditions employed. For example, in some variations, carbonylation can result in the formation of a beta lactone as shown in the following general reaction:

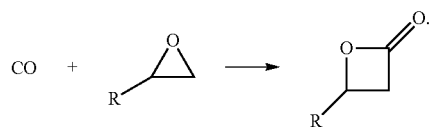

Exemplary reactions include:

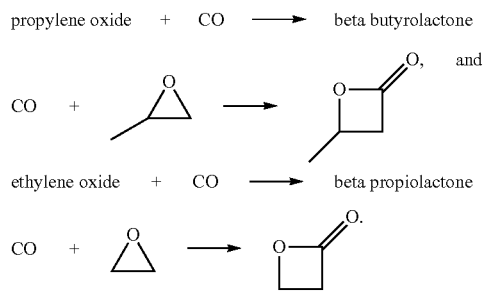

In other variations, carbonylation can result in the formation of a polyester as shown in the following general reaction:

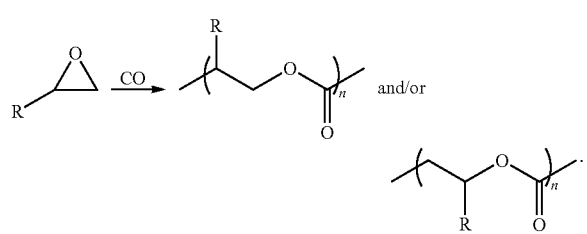

Exemplary reactions include:

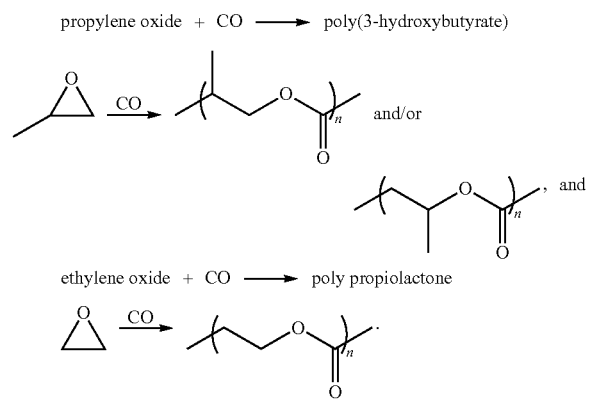

In yet other variations, carbonylation results in the formation of a succinic anhydride by insertion of two molecules of CO. Such processes conform to the general reaction scheme:

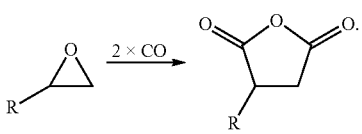

Exemplary reactions include:

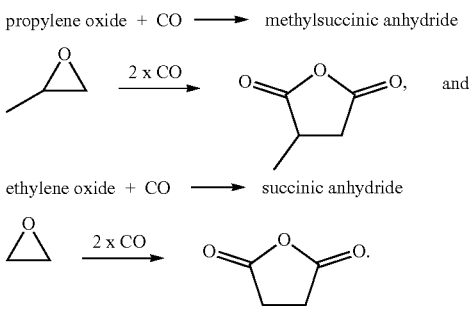

Any suitable epoxides may be used in the methods described herein. No particular constraints are placed on the identity of the epoxide used in the carbonylation reactions described herein. In some embodiments, the epoxide is selected from the group consisting of ethylene oxide, propylene oxide, 1,2-butylene oxide, 2,3-butylene oxide, epichlorohydrin, cyclohexene oxide, cyclopentene oxide, 3,3,3-Trifluoro-1,2-epoxypropane, styrene oxide, a glycidyl ether, and a glycidyl ester. In some embodiments, the epoxide is propylene oxide. In some embodiments, the epoxide is ethylene oxide. In one variation when the epoxide is ethylene oxide, the carbonylation product is beta propriolactone. In another variation when the epoxide is ethylene oxide, the carbonylation product is succinic anhydride.

In some embodiments, the epoxide is ethylene oxide which is obtained directly from the gas phase oxidation of ethylene. This embodiment is advantageous in that it avoids the need to isolate, store, and transport ethylene oxide which is both toxic and explosive. In some embodiments, the ethylene oxide is maintained in the gas phase as produced and fed to the carbonylation reaction without condensing it to a liquid.

Lactones

In other variations, the methods herein involve the continuous carbonylation of lactones. For example, in some variations, carbonylation of a beta lactone can result in the formation of a succinic anhydride product, as shown in the following general reaction:

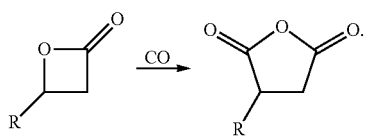

An example reaction includes:

beta propiolactone + CO → succinic anhydride

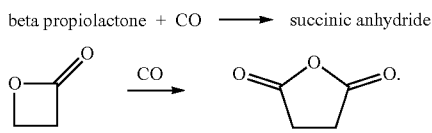

In some embodiments, the lactone is beta propriolactone. In one variation when the lactone is beta propriolactone, the carbonylation product is succinic anhydride.

Carbon Monoxide

Carbon monoxide (also referred to as "CO") can be provided either as a pure stream or as a mixture of carbon monoxide and one or more additional gases. In some embodiments, carbon monoxide is provided in a mixture with hydrogen (e.g., Syngas). The ratio of carbon monoxide and hydrogen can be any ratio, including for example 1:1, 1:2, 1:4, 1:10, 10:1, 4:1, or 2:1 or within any range with these ratios as end points. In some embodiments, the carbon monoxide is provided in mixture with gases as an industrial process gas. The carbon monoxide sources include for example wood gas, producer gas, coal gas, town gas, manufactured gas, hygas, Dowson gas or water gas, among others. In some embodiments, the carbon monoxide is provided at super-atmospheric pressure.

Feedstock Streams

In some embodiments, the feedstock stream fed into the carbonylation reaction comprises a gaseous mixture containing epoxide and carbon monoxide. In some embodiments, the molar ratio of carbon monoxide to epoxide in the feedstock stream ranges from about 1:1 to about 10,000:1. In some embodiments, the molar ratio of carbon monoxide to epoxide in the feedstock stream is about 5000:1, is about 2500:1, is about 2000:1, is about 1500:1, is about 1000:1, is about 500:1, is about 1:500, is about 200:1, is about 100:1, is about 50:1, is about 20:1, is about 10:1, is about 5:1 or is about 1:1. In some embodiments, the ratio of carbon monoxide to epoxide is selected, based on other reaction conditions, so that the reaction proceeds in an economical and time-feasible manner. In some embodiments, the ratio of carbon monoxide to epoxide in the feedstock stream is between about 1:1 to about 100:1. In some embodiments, the ratio of carbon monoxide to epoxide in the feedstock stream is between about 1:1 to about 1000:1. In some embodiments, the ratio of carbon monoxide to epoxide in the feedstock stream is between about 10:1 to about 1000:1. In some embodiments, the ratio of carbon monoxide to epoxide in the feedstock stream is between about 10:1 to about 10,000:1. In some embodiments, the ratio of carbon monoxide to epoxide in the feedstock stream is between about 100:1 to about 1000:1. In some embodiments, the ratio of carbon monoxide to epoxide in the feedstock stream is between about 10:1 to about 1000:1. In some embodiments, the ratio of carbon monoxide to epoxide in the feedstock stream is between about 10:1 to about 500:1. In some embodiments, the ratio of carbon monoxide to epoxide in the feedstock stream is between about 10:1 to about 100:1. In some embodiments, the ratio of carbon monoxide to epoxide in the feedstock stream is between about 10:1 to about 50:1. In some embodiments, the ratio of carbon monoxide to epoxide in the feedstock stream is between about 20:1 to about 200:1. In some embodiments, the ratio of carbon monoxide to epoxide in the feedstock stream is between about 50:1 to about 200:1.

In some embodiments, the feedstock stream further comprises one or more additional components. In some embodiments, the additional components comprise diluents which do not directly participate in the chemical reactions of the epoxide or the products of those reactions. In some embodiments, such diluents may include one or more inert gases (e.g., nitrogen, argon, and helium) or volatile organic molecules such as hydrocarbons, and ethers. In some embodiments, the feedstock stream may comprise hydrogen, traces of carbon dioxide, methane, and other compounds commonly found in industrial carbon monoxide streams. In some embodiments, the feed stream may further comprise materials that may have a direct or indirect chemical function in one or more of the processes involved in the conversion of the epoxide to various end products. Additional reactants can also include mixtures of carbon monoxide and another gas. For example, as noted above, in some embodiments, carbon monoxide is provided in a mixture with hydrogen (e.g., syngas).

In some embodiments, the feedstock stream is characterized in that it is essentially free of oxygen. In some embodiments, the feedstock stream is characterized in that it is essentially free of water. In some embodiments, the feedstock stream is characterized in that it is essentially free of oxygen and water.

Enumerated Embodiments

The following enumerated embodiments are representative of some aspects of the invention.

1. A process for continuous carbonylation of an epoxide or lactone feedstock, comprising:

reacting an epoxide or lactone feedstock with carbon monoxide in the presence of a catalyst comprising a Lewis acid and a metal carbonyl in a carbonylation reaction vessel;

measuring one or more parameters selected from the group consisting of:

i) a concentration of the Lewis acid, or a decomposition product thereof, within the carbonylation reaction vessel;

ii) a concentration of the Lewis acid, or a decomposition product thereof, in a product stream downstream from the carbonylation reaction vessel;

iii) a concentration of the metal carbonyl, or a decomposition product thereof, within the carbonylation reaction vessel;

iv) a concentration of the metal carbonyl, or a decomposition product thereof, in a product stream downstream from the carbonylation reaction vessel; and v) a rate of the carbonylation reaction;

comparing the measured value of the one or more parameters to predetermined reference values for the one or more parameters; and where the measured value of any one of parameters i), iii), or v) is less than the reference value, or where the measured value of any one of parameters ii) or iv) is greater than the reference value, introducing to the carbonylation reaction vessel a catalyst replacement component which is different from the catalyst and comprises a species selected from the group consisting of the Lewis acid, a precursor to the Lewis acid, the metal carbonyl, and a precursor to the metal carbonyl.

2. The process of embodiment 1, wherein the product stream is separated from the carbonylation reaction vessel by a nanofiltration membrane.

3. The process of any one of the previous embodiments, wherein the nanofiltration membrane is designed to retain solutes having a molecular weight greater than the molecular weight of the epoxide or lactone carbonylation products, and to allow solutes having lower molecular weights to permeate.

4. The process of any one of the previous embodiments, wherein the precursor to the metal carbonyl is a neutral metal carbonyl complex.

5. The process of any one of the previous embodiments, wherein the precursor to the metal carbonyl is $Co_2(CO)_8$ or $Co_4(CO)_{12}$.

6. The process of any one of the previous embodiments, wherein the concentration of the Lewis acid, or a decomposition product thereof, is measured by IR, UV, or NMR.

7. The process of any one of the previous embodiments, wherein the concentration of the metal carbonyl, or a decomposition product there is measured by IR, UV, or NMR.

8. The process of any one of the previous embodiments, wherein the catalyst replacement component is introduced directly to the carbonylation reaction vessel.

9. The process of any one of the previous embodiments, wherein the catalyst replacement component is recycled from the product stream.

10. The process of any one of the previous embodiments, wherein the one or more parameters are measured continuously.

11. The process of any one of the previous embodiments, wherein the catalyst replacement component is added continuously.

12. The process of any one of the previous embodiments, wherein the catalyst replacement component is added intermittently.

13. The process of any one of the previous embodiments, wherein the Lewis acid is cationic.

14. The process of any one of the previous embodiments, wherein the metal carbonyl is anionic.

15. A process for continuous carbonylation of an epoxide or lactone feedstock, the process comprising the steps of:

reacting an epoxide or lactone feedstock with carbon monoxide in the presence of a catalyst comprising a Lewis acid and a metal carbonyl in a carbonylation reaction vessel; and continuously or intermittently introducing to the carbonylation reaction vessel a catalyst replacement component which is different from the catalyst and comprises a species selected from the group consisting of the Lewis acid, a precursor to the Lewis acid, the metal carbonyl, and a precursor to the metal carbonyl.

16. The process of embodiment 15, wherein the catalyst replacement component is introduced at a rate that results in less than 10% variation in the rate of the carbonylation reaction over a period of one hour.

17. The process of any one of the previous embodiments, wherein the Lewis acid is of formula I:

I wherein:

is a multidentate ligand;

M is a metal atom coordinated to the multidentate ligand; and a is the charge of the metal atom and ranges from 0 to 2.

18. The process of any one of embodiments 1-16, wherein the Lewis acid is of formula II:

II wherein:

$M^1$ is a first metal atom;
$M^2$ is a second metal atom;
each a is the charge of the metal atom and independently ranges from 0 to 2; and

comprises a multidentate ligand system capable of coordinating both metal atoms.

19. The process of embodiment 17, wherein the precursor to the Lewis acid is of the formula:

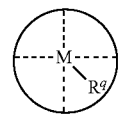

wherein:

is a multidentate ligand;

M is a metal atom coordinated to the multidentate ligand; and

R^q is selected from $C_{1-12}$ aliphatic and optionally substituted aryl.

20. The process of embodiment 18, wherein the precursor to the Lewis acid is of the formula:

wherein:
M¹ is a first metal atom;
M² is a second metal atom;

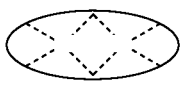

comprises a multidentate ligand system capable of coordinating both metal atoms; and
each $R^q$ is independently selected from $C_{1-12}$ aliphatic and optionally substituted aryl.

21. A process for continuous carbonylation of an epoxide or lactone feedstock, comprising:
continuously reacting an epoxide or lactone feedstock with carbon monoxide in the presence of a carbonylation catalyst in a carbonylation reaction vessel,
wherein the carbonylation catalyst comprises a Lewis acid and a metal carbonyl, and
wherein at a start time of the process, the carbonylation reaction vessel contains an initial concentration of the Lewis acid and an initial concentration of the metal carbonyl; and
adding to the carbonylation reaction vessel, at a time after the start time of the process, a catalyst replacement component which is different from the catalyst,
wherein the catalyst replacement component comprises the Lewis acid, a precursor to the Lewis acid, the metal carbonyl, and a precursor to the metal carbonyl.

22. The process of embodiment 21, wherein a rate or time of addition of the catalyst replacement component is based on a rate of depletion of one or both of the Lewis acid and the metal carbonyl in the carbonylation reaction vessel.

23. The process of embodiment 22, wherein one or both of the Lewis acid and the metal carbonyl of the carbonylation catalyst depletes over time in the carbonylation reaction vessel, and the method further comprises determining the depletion.

24. The process of embodiment 23, wherein the depletion of one or both of the Lewis acid and the metal carbonyl in the carbonylation reaction vessel is determined by:
measuring one or more parameters selected from the group consisting of:
i-a) a concentration of the Lewis acid in the carbonylation reaction vessel;
i-b) a concentration of a decomposition product of the Lewis acid in the carbonylation reaction vessel;
ii-a) a concentration of the Lewis acid in a process stream downstream from the carbonylation reaction vessel;
ii-b) a concentration of a decomposition product of the Lewis acid in a process stream downstream from the carbonylation reaction vessel;
iii-a) a concentration of the metal carbonyl in the carbonylation reaction vessel;
iii-b) a concentration of a decomposition product of the metal carbonyl in the carbonylation reaction vessel;
iv-a) a concentration of the metal carbonyl in a process stream downstream from the carbonylation reaction vessel;
iv-b) a concentration of a decomposition product of the metal carbonyl in a process stream downstream from the carbonylation reaction vessel; and
v) a rate of the carbonylation reaction; and
obtaining a measured value of the one or more parameters.

25. The process of embodiment 24, further comprising:
comparing the measured value of the one or more parameters to a predetermined reference value for each parameter; and
determining a rate of addition or a time of addition of the catalyst replacement component based on the comparison.

26. The process of embodiment 25, wherein the rate of addition of the metal carbonyl or a precursor to the metal carbonyl is increased when the value of a measurement in parameter iii-b, iv-a, or iv-b, or any combination thereof, is greater than the predetermined value for each parameter.

27. The process of embodiment 25, wherein the rate of addition of the metal carbonyl or a precursor to the metal carbonyl is increased when the value of a measurement in parameter iii-a is less than the predetermined value for the parameter.

28. The process of embodiment 25, wherein the rate of addition of the Lewis acid or a precursor to the Lewis Acid is increased when the value of a measurement in parameter i-b, ii-a, or ii-b, or any combination thereof, is greater than the predetermined value for each parameter.

29. The process of embodiment 25, wherein the rate of addition of the Lewis acid or a precursor to the Lewis acid is increased when the value of a measurement in parameter i-a is less than the predetermined value for the parameter.

30. The process of any one of embodiments 21 to 29, wherein the reacting of the epoxide or lactone feedstock with the carbon monoxide in the presence of the carbonylation catalyst in the carbonylation reaction vessel produces carbonylation products in a carbonylation product stream, and
the process further comprises separating the carbonylation product stream from the carbonylation reaction vessel.

31. The process of embodiment 30, wherein the carbonylation product stream is separated from the carbonylation reaction vessel by a nanofiltration membrane.

32. The process of embodiment 31, wherein the nanofiltration membrane retains at least a portion of the Lewis acid and the metal carbonyl, and permeates the carbonylation products.

33. The process of any one of embodiments 21 to 32, wherein the precursor to the metal carbonyl is a neutral metal carbonyl complex.

34. The process of any one of embodiments 21 to 33, wherein the precursor to the metal carbonyl is $Co_2(CO)_8$ or $Co_4(CO)_{12}$.

35. The process of any one of embodiments 24 to 34, wherein the concentration of the Lewis acid, or a decomposition product thereof, is measured by spectroscopy.

36. The process of any one of embodiments 24 to 35, wherein the concentration of the Lewis acid, or a decomposition product thereof, is measured by IR, UV, mass or NMR spectroscopy.

37. The process of any one of embodiments 24 to 36, wherein the concentration of the metal carbonyl, or a decomposition product thereof, is measured by spectroscopy.

38. The process of any one of embodiments 24 to 36, wherein the concentration of the metal carbonyl, or a decomposition product thereof, is measured by IR, UV, mass or NMR spectroscopy.

39. The process of any one of embodiments 21 to 38, wherein the catalyst replacement component is added directly to the carbonylation reaction vessel.

40. The process of any one of embodiments 21 to 38, wherein the catalyst replacement component is recycled from a carbonylation product stream, an intermediate carbonylation process stream, or a process stream downstream of the carbonylation reaction vessel.

41. The process of any one of embodiments 24 to 40, wherein the one or more parameters are measured continuously.

42. The process of any one of embodiments 21 to 41, wherein the catalyst replacement component is added continuously.

43. The process of any one of embodiments 21 to 41, wherein the catalyst replacement component is added intermittently.

44. The process of any one of embodiments 21 to 43, wherein the Lewis acid is cationic.

45. The process of any one of embodiments 21 to 44, wherein the metal carbonyl is anionic.

46. A process for continuous carbonylation of an epoxide or lactone feedstock, comprising:
continuously reacting an epoxide or lactone feedstock with carbon monoxide in the presence of a catalyst in a carbonylation reaction vessel, wherein the catalyst comprises a Lewis acid and a metal carbonyl; and
continuously or intermittently introducing to the carbonylation reaction vessel a catalyst replacement component which is different from the catalyst, wherein the catalyst replacement component comprises a species selected from the group consisting of the Lewis acid, a precursor to the Lewis acid, the metal carbonyl, and a precursor to the metal carbonyl.

47. The process of embodiment 46, wherein the catalyst replacement component is introduced at a rate that results in less than 10% variation in the rate of the carbonylation reaction over a period of one hour.

48. The process of any one of embodiments 21 to 47, wherein the Lewis acid is of formula I:

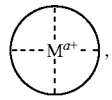

wherein:

is a multidentate ligand;
M is a metal atom coordinated to the multidentate ligand; and
a is the charge of the metal atom and ranges from 0 to 2.

49. The process of any one of embodiments 21 to 47, wherein the Lewis acid is of formula II:

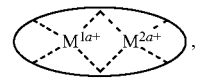

wherein:
M$^1$ is a first metal atom;
M$^2$ is a second metal atom;
each a is the charge of the metal atom and independently ranges from 0 to 2; and

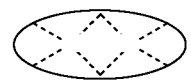

comprises a multidentate ligand system capable of coordinating both metal atoms.

50. The process of embodiment 48, wherein the precursor to the Lewis acid is of the formula:

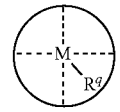

wherein:
⊕ is a multidentate ligand;
M is a metal atom coordinated to the multidentate ligand; and
R$^q$ is selected from C$_{1-12}$ aliphatic and optionally substituted aryl.

51. The process of embodiment 49, wherein the precursor to the Lewis acid is of the formula:

wherein:
M$^1$ is a first metal atom;
M$^2$ is a second metal atom;

comprises a multidentate ligand system capable of coordinating both metal atoms; and
each R$^q$ is independently selected from C$_{1-12}$ aliphatic and optionally substituted aryl.

52. The process of any one of embodiments 21 to 51, wherein the epoxide feedstock is continuously reacted with the carbon monoxide in the presence of the carbonylation catalyst in the carbonylation reaction vessel.

53. The process of any one of embodiments 21 to 52, wherein the epoxide feedstock comprises ethylene oxide.

54. The process of any one of embodiments 21 to 53, wherein continuously reacting the epoxide or lactone feedstock with the carbon monoxide in the presence of the carbonylation catalyst produces beta-propiolactone.

55. The process of any one of embodiments 21 to 53, wherein continuously reacting the epoxide or lactone feedstock with the carbon monoxide in the presence of the carbonylation catalyst produces succinic anhydride.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A process for continuous carbonylation of an epoxide or lactone feedstock, comprising:

continuously reacting an epoxide or lactone feedstock with carbon monoxide in the presence of a carbonylation catalyst in a carbonylation reaction vessel, wherein the carbonylation catalyst comprises a Lewis acid and a metal carbonyl, and wherein at a start time of the process, the carbonylation reaction vessel contains an initial concentration of the Lewis acid and an initial concentration of the metal carbonyl; and adding to the carbonylation reaction vessel, at a time after the start time of the process, a catalyst replacement component which is different from the carbonylation catalyst, wherein the catalyst replacement component comprises the Lewis acid, a precursor to the Lewis acid, the metal carbonyl, and a precursor to the metal carbonyl, wherein the precursor to the metal carbonyl is a neutral metal carbonyl complex, and wherein the precursor to the Lewis acid is:

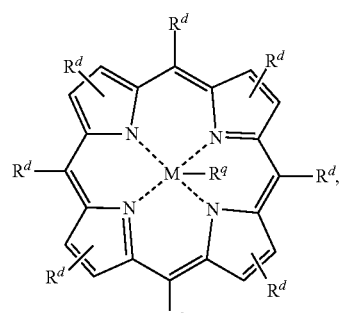

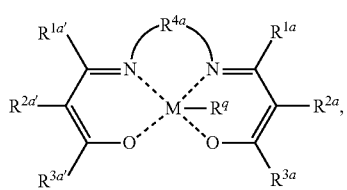

-continued

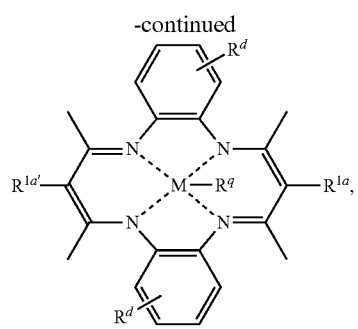

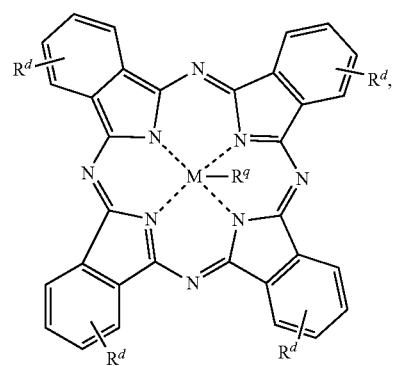

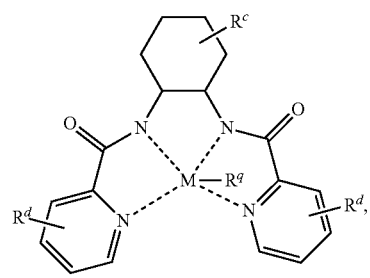

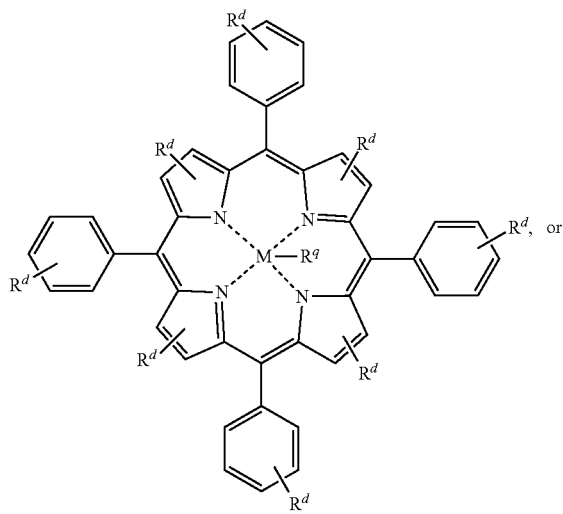

-continued

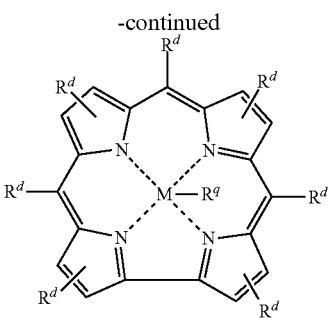

wherein:
each $R^q$ is independently $C_{1-12}$ aliphatic or aryl,
wherein the aryl is unsubstituted or substituted with one or more substituents selected from the group consisting of halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$; —$(CH_2)_{0-4}O(CH_2)_{0-1}Ph$; —CH=CHPh; —$NO_2$; —CN; —$N_3$; —$(CH_2)_{0-4}N(R°)_2$; —$(CH_2)_{0-4}N(R°C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)N(R°)_2$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR°$; —SC(S)SR°; —$(CH_2)_{0-4}SC(O)R°$; —$(CH_2)_{0-4}C(O)NR°_2$; —$C(S)NR°_2$; —$C(S)SR°$, —SC(S)SR°; —$(CH_2)_{0-4}OC(O)NR°_2$; —C(O)N(OR°)R°, —C(O)C(O)R°, —C(O)CH_2C(O)R°; —C(NOR°)R°; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —S(O)_2NR°_2; —$(CH_2)_{0-4}S(O)R°$; —$N(R°)S(O)_2NR°_2$; —$N(R°)S(O)_2R°$; —$N(OR°)R°$; —C(NH)NR°_2; —P(O)_2R°; —P(O)R°_2; —OP(O)R°_2; —OP(O)(OR°)_2; SiR°_3; —($C_{1-4}$ straight or branched alkylene)O—N(R°)_2; and —($C_{1-4}$ straight or branched alkylene)C(O)O—N(R°)_2,
wherein R° at each occurrence is
independently hydrogen, $C_{1-8}$ aliphatic, —$CH_2Ph$, or —$O(CH_2)_{0-1}Ph$; or
a 5-6-membered saturated, partially unsaturated, or aryl ring having 0-4 heteroatoms independently selected from nitrogen, oxygen, and sulfur; or
wherein two independent occurrences of R°, taken together with their intervening atom(s), form a 3-12-membered saturated, partially unsaturated, or aryl mono- or polycyclic ring having 0-4 heteroatoms independently selected from nitrogen, oxygen, and sulfur;
M is a metal atom;
$R^d$ at each occurrence is
independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, or —$SiR^y_3$; or an optionally substituted group selected from the group consisting of:
$C_{1-20}$ aliphatic;
$C_{1-20}$ heteroaliphatic having 1-4 heteroatoms independently selected from the group consisting of nitrogen, oxygen, and sulfur;
6- to 10-membered aryl;
5- to 10-membered heteroaryl having 1-4 heteroatoms independently selected from nitrogen, oxygen, and sulfur; and
4- to 7-membered heterocyclic having 1-2 heteroatoms independently selected from the group consisting of nitrogen, oxygen, and sulfur; or
wherein two or more $R^d$ groups may be taken together to form one or more optionally substituted rings;
each $R^y$ is
independently hydrogen; or an optionally substituted group selected the group consisting of:
acyl;
carbamoyl,
arylalkyl;
6- to 10-membered aryl;
$C_{1-12}$ aliphatic;
$C_{1-12}$ heteroaliphatic having 1-2 heteroatoms independently selected from the group consisting of nitrogen, oxygen, and sulfur;
5- to 10-membered heteroaryl having 1-4 heteroatoms independently selected from the group consisting of nitrogen, oxygen, and sulfur;
4- to 7-membered heterocyclic having 1-2 heteroatoms independently selected from the group consisting of nitrogen, oxygen, and sulfur;
an oxygen protecting group; and
a nitrogen protecting group; or
wherein two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and
each $R^4$ is independently a hydroxyl protecting group or $R^y$;
$R^{1a}$, $R^{1a'}$, $R^{2a}$, $R^{2a'}$, $R^{3a}$, and $R^{3a'}$ are
independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, or —$SiR^y_3$; or an optionally substituted group selected from the group consisting of:
$C_{1-20}$ aliphatic;
$C_{1-20}$ heteroaliphatic having 1-4 heteroatoms independently selected from the group consisting of nitrogen, oxygen, and sulfur;
6- to 10-membered aryl;
5- to 10-membered heteroaryl having 1-4 heteroatoms independently selected from nitrogen, oxygen, and sulfur; and
4- to 7-membered heterocyclic having 1-2 heteroatoms independently selected from the group consisting of nitrogen, oxygen, and sulfur; or
wherein any of ($R^{2a'}$ and $R^{3'}$), ($R^{2a}$ and $R^{3a}$), ($R^{1a}$ and $R^{2a}$), and ($R^{1a'}$ and $R^{2'}$) may optionally be taken together with the carbon atoms to which they are attached to form one or more rings which may in turn be substituted with one or more $R^y$ groups; and
$R^{4a}$ is selected from the group consisting of:

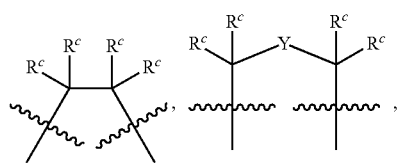

-continued

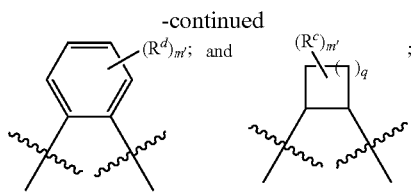

wherein:
R$^c$ at each occurrence is
independently hydrogen, halogen, —OR$^4$, —NR$^y_2$, —SR$^y$, —CN, —NO$_2$, —SO$_2$R$^y$, —SOR$^y$, —SO$_2$NR$^y_2$; —CNO, —NR$^y$SO$_2$R$^y$, —NCO, —N$_3$, or —SiR$^y_3$; or an optionally substituted group selected from the group consisting of:
C$_{1-20}$ aliphatic;
C$_{1-20}$ heteroaliphatic having 1-4 heteroatoms independently selected from the group consisting of nitrogen, oxygen, and sulfur;
6- to 10-membered aryl;
5- to 10-membered heteroaryl having 1-4 heteroatoms independently selected from nitrogen, oxygen, and sulfur; and
4- to 7-membered heterocyclic having 1-2 heteroatoms independently selected from the group consisting of nitrogen, oxygen, and sulfur; or
wherein two or more R$^c$ groups may be taken together with the carbon atoms to which they are attached and any intervening atoms to form one or more rings; or
wherein two R$^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;
Y is a divalent linker selected from the group consisting of: —NR$^y$—, —N(R$^y$)C(O)—, —C(O)NR$^y$—, —O—, —C(O)—, —OC(O)—, —C(O)O—, —S—, —SO—, —SO$_2$—, —C(=S)—, —C(=NR$^y$)—, —N=N—; a polyether; a C$_3$ to C$_8$ substituted or unsubstituted carbocycle; and a C$_1$ to C$_8$ substituted or unsubstituted heterocycle;
m' is 0 or an integer from 1 to 4, inclusive; and
q is 0 or an integer from 1 to 4, inclusive.

2. The process of claim 1, wherein a rate or time of addition of the catalyst replacement component is based on a rate of depletion of one or both of the Lewis acid and the metal carbonyl in the carbonylation reaction vessel.

3. The process of claim 2, wherein one or both of the Lewis acid and the metal carbonyl of the carbonylation catalyst depletes over time in the carbonylation reaction vessel, and the method further comprises determining the depletion,
wherein the depletion of one or both of the Lewis acid and the metal carbonyl in the carbonylation reaction vessel is determined by:
measuring one or more parameters selected from the group consisting of:
i-a) a concentration of the Lewis acid in the carbonylation reaction vessel;
i-b) a concentration of a decomposition product of the Lewis acid in the carbonylation reaction vessel;
ii-a) a concentration of the Lewis acid in a process stream downstream from the carbonylation reaction vessel;
ii-b) a concentration of a decomposition product of the Lewis acid in a process stream downstream from the carbonylation reaction vessel;
iii-a) a concentration of the metal carbonyl in the carbonylation reaction vessel;
iii-b) a concentration of a decomposition product of the metal carbonyl in the carbonylation reaction vessel;
iv-a) a concentration of the metal carbonyl in a process stream downstream from the carbonylation reaction vessel;
iv-b) a concentration of a decomposition product of the metal carbonyl in a process stream downstream from the carbonylation reaction vessel; and
v) a rate of the carbonylation reaction; and
obtaining a measured value of the one or more parameters.

4. The process of claim 3, further comprising:
comparing the measured value of the one or more parameters to a predetermined reference value for each parameter; and
determining a rate of addition or a time of addition of the catalyst replacement component based on the comparison.

5. The process of claim 4, wherein:
the rate of addition of the metal carbonyl or a precursor to the metal carbonyl is increased when the value of a measurement in parameter iii-b, iv-a, or iv-b, or any combination thereof, is greater than the predetermined value for each parameter;
the rate of addition of the metal carbonyl or a precursor to the metal carbonyl is increased when the value of a measurement in parameter iii-a is less than the predetermined value for the parameter;
the rate of addition of the Lewis acid or a precursor to the Lewis Acid is increased when the value of a measurement in parameter i-b, ii-a, or ii-b, or any combination thereof, is greater than the predetermined value for each parameter; and
the rate of addition of the Lewis acid or a precursor to the Lewis acid is increased when the value of a measurement in parameter i-a is less than the predetermined value for the parameter.

6. The process of claim 1, wherein the reacting of the epoxide or lactone feedstock with the carbon monoxide in the presence of the carbonylation catalyst in the carbonylation reaction vessel produces carbonylation products in a carbonylation product stream, and
the process further comprises separating the carbonylation product stream from the carbonylation reaction vessel.

7. The process of claim 6, wherein the carbonylation product stream is separated from the carbonylation reaction vessel by a nanofiltration membrane, and wherein the nanofiltration membrane retains at least a portion of the Lewis acid and the metal carbonyl, and permeates the carbonylation products.

8. The process of claim 1, wherein the precursor to the metal carbonyl is Co$_2$(CO)$_8$ or Co$_4$(CO)$_{12}$.

9. The process of claim 1, wherein the catalyst replacement component is added directly to the carbonylation reaction vessel.

10. The process of claim 1, wherein the catalyst replacement component is recycled from a carbonylation product stream, an intermediate carbonylation process stream, or a process stream downstream of the carbonylation reaction vessel.

11. The process of claim 3, wherein the one or more parameters are measured continuously.

12. The process of claim 1, wherein the catalyst replacement component is added continuously.

13. The process of claim 1, wherein the catalyst replacement component is added intermittently.

14. A process for continuous carbonylation of an epoxide or lactone feedstock, comprising:
continuously reacting an epoxide or lactone feedstock with carbon monoxide in the presence of a catalyst in a carbonylation reaction vessel, wherein the catalyst comprises a Lewis acid and a metal carbonyl; and
continuously or intermittently introducing to the carbonylation reaction vessel a catalyst replacement component which is different from the carbonylation catalyst, wherein the catalyst replacement component comprises a species selected from the group consisting of the Lewis acid, a precursor to the Lewis acid, the metal carbonyl, and a precursor to the metal carbonyl,
wherein the precursor to the metal carbonyl is a neutral metal carbonyl complex, and
wherein the precursor to the Lewis acid is:

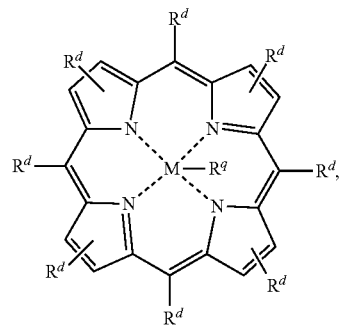

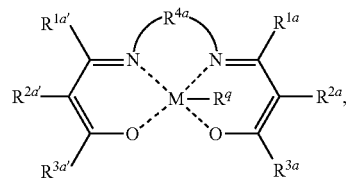

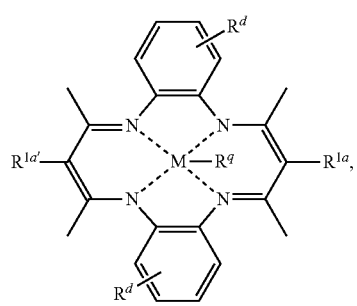

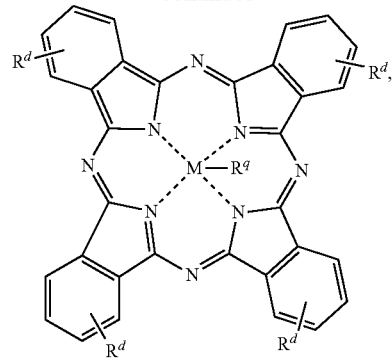

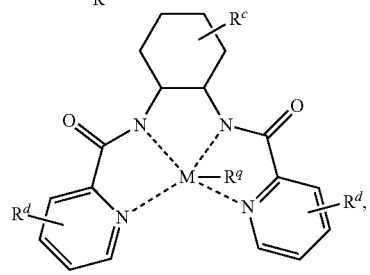

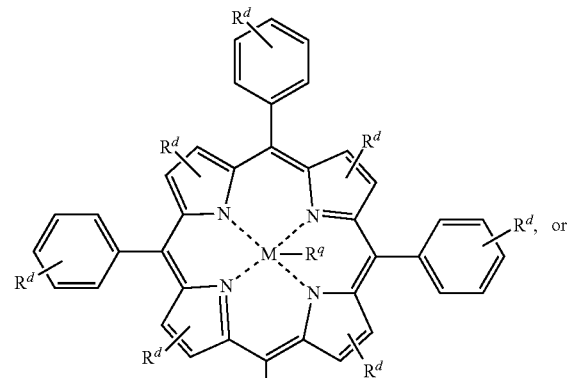

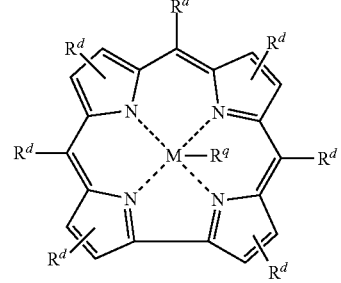

wherein:
each $R^q$ is independently $C_{1-12}$ aliphatic or aryl,
wherein the aryl is unsubstituted or substituted with one or more substituents selected from the group consisting of halogen; $-(CH_2)_{0-4}R°$; $-(CH_2)_{0-4}OR°$; $-O-(CH_2)_{0-4}C(O)OR°$; $-(CH_2)_{0-4}CH(OR°)_2$; $-(CH_2)_{0-4}SR°$; $-(CH_2)_{0-4}Ph$; $-(CH_2)_{0-4}O(CH_2)_{0-1}Ph$; $-CH=CHPh$; $-NO_2$; $-CN$; $-N_3$; $-(CH_2)_{0-4}N(R°)_2$; $-(CH_2)_{0-4}N(R°C(O)R°$; $-N(R°)C(S)R°$; $-(CH_2)_{0-4}N(R°)C(O)NR°_2$; $-N(R°)C(S)NR°_2$; $-(CH_2)_{0-4}N(R°)C(O)OR°$;

—N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)N(R°)$_2$; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —SC(S)SR°; —(CH$_2$)$_{0-4}$SC(O)R°; —(CH$_2$)$_{0-4}$C(O)NR°$_2$; —C(S)NR°$_2$; —C(S)SR°, —SC(S)SR°; —(CH$_2$)$_{0-4}$OC(O)NR°$_2$; —C(O)N(OR°)R°, —C(O)C(O)R°, —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; and —(C$_{1-4}$ straight or branched alkylene)C(O)O—N(R°)$_2$, wherein R° at each occurrence is independently hydrogen, C$_{1-8}$ aliphatic, —CH$_2$Ph or —O(CH$_2$)$_{0-1}$Ph; or a 5-6-membered saturated, partially unsaturated, or aryl ring having 0-4 heteroatoms independently selected from nitrogen, oxygen, and sulfur; or wherein two independent occurrences of R°, taken together with their intervening atom(s), form a 3-12-membered saturated, partially unsaturated, or aryl mono- or polycyclic ring having 0-4 heteroatoms independently selected from nitrogen, oxygen, and sulfur;

M is a metal atom;

R$^d$ at each occurrence is independently hydrogen, halogen, —OR$^4$, —NR$^y$$_2$, —SR$^y$, —CN, —NO$_2$, —SO$_2$R$^y$, —SOR$^y$, —SO$_2$NR$^y$$_2$; —CNO, —NR$^y$SO$_2$R$^y$, —NCO, —N$_3$, or —SiR$^y$$_3$; or an optionally substituted group selected from the group consisting of:

C$_{1-20}$ aliphatic;

C$_{1-20}$ heteroaliphatic having 1-4 heteroatoms independently selected from the group consisting of nitrogen, oxygen, and sulfur;

6- to 10-membered aryl;

5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; or wherein two or more R$^d$ groups may be taken together to form one or more optionally substituted rings;

each R$^y$ is independently hydrogen; or an optionally substituted group selected the group consisting of:

acyl;

carbamoyl, arylalkyl;

6- to 10-membered aryl;

C$_{1-12}$ aliphatic;

C$_{1-12}$ heteroaliphatic having 1-2 heteroatoms independently selected from the group consisting of nitrogen, oxygen, and sulfur;

5- to 10-membered heteroaryl having 1-4 heteroatoms independently selected from the group consisting of nitrogen, oxygen, and sulfur;

4- to 7-membered heterocyclic having 1-2 heteroatoms independently selected from the group consisting of nitrogen, oxygen, and sulfur;

an oxygen protecting group; and a nitrogen protecting group; or wherein two R$^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each R$^4$ is independently a hydroxyl protecting group or R$^y$;

R$^{1a}$, R$^{1a'}$, R$^{2a}$, R$^{2a'}$, R$^{3a}$, and R$^{3a'}$ are independently hydrogen, halogen, —OR$^4$, —NR$^y$$_2$, —SR$^y$, —CN, —NO$_2$, —SO$_2$R$^y$, —SOR$^y$, —SO$_2$NR$^y$$_2$; —CNO, —NR$^y$SO$_2$R$^y$, —NCO, —N$_3$, or —SiR$^y$$_3$; or an optionally substituted group selected from the group consisting of:

C$_{1-20}$ aliphatic;

C$_{1-20}$ heteroaliphatic having 1-4 heteroatoms independently selected from the group consisting of nitrogen, oxygen, and sulfur;

6- to 10-membered aryl;

5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; or wherein any of (R$^{2a'}$ and R$^{3'}$), (R$^{2a}$ and R$^{3a}$), (R$^{1a}$ and R$^{2a}$), and (R$^{1a'}$ and R$^{2'}$) may optionally be taken together with the carbon atoms to which they are attached to form one or more rings which may in turn be substituted with one or more R$^y$ groups; and R$^{4a}$ is selected from the group consisting of:

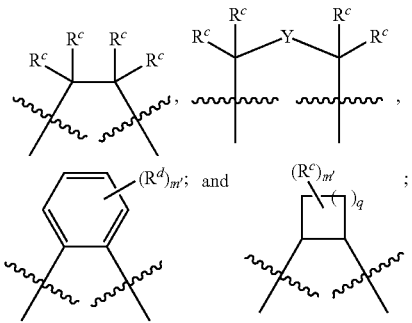

wherein:

R$^c$ at each occurrence is independently hydrogen, halogen, —OR$^4$, —NR$^y$$_2$, —SR$^y$, —CN, —NO$_2$, —SO$_2$R$^y$, —SOR$^y$, —SO$_2$NR$^y$$_2$; —CNO, —NR$^y$SO$_2$R$^y$, —NCO, —N$_3$, or —SiR$^y$$_3$; or an optionally substituted group selected from the group consisting of:

C$_{1-20}$ aliphatic;

C$_{1-20}$ heteroaliphatic having 1-4 heteroatoms independently selected from the group consisting of nitrogen, oxygen, and sulfur;

6- to 10-membered aryl;

5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; or wherein two or more R^c groups may be taken together with the carbon atoms to which they are attached and any intervening atoms to form one or more rings; or wherein two R^c groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;

Y is a divalent linker selected from the group consisting of: —NR^y—, —N(R^y)C(O)—, —C(O)NR^y—, —O—, —C(O)—, —OC(O)—, —C(O)O—, —S—, —SO—, —SO_2—, —C(=S)—, —C(=NR^y)—, —N=N—; a polyether; a $C_3$ to $C_8$ substituted or unsubstituted carbocycle; and a $C_1$ to $C_8$ substituted or unsubstituted heterocycle;

m' is 0 or an integer from 1 to 4, inclusive; and q is 0 or an integer from 1 to 4, inclusive.

15. The process of claim 14, wherein the catalyst replacement component is introduced at a rate that results in less than 10% variation in the rate of the carbonylation reaction over a period of one hour.

16. The process of claim 1, wherein the epoxide feedstock is continuously reacted with the carbon monoxide in the presence of the carbonylation catalyst in the carbonylation reaction vessel.

17. The process of claim 1, wherein the epoxide feedstock comprises ethylene oxide.

18. The process of claim 1, wherein the precursor to the Lewis acid is

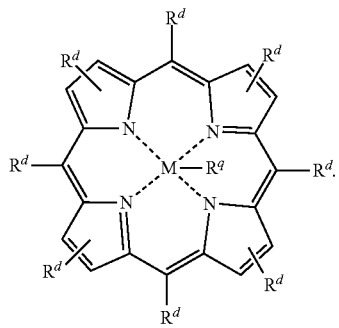

19. The process of claim 1, wherein the precursor to the Lewis acid is

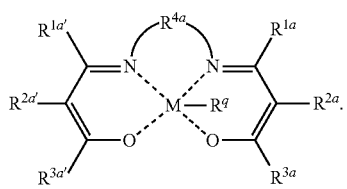

20. The process of claim 1, wherein the precursor to the Lewis acid is

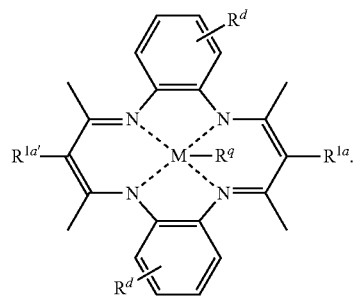

21. The process of claim 1, wherein the precursor to the Lewis acid is

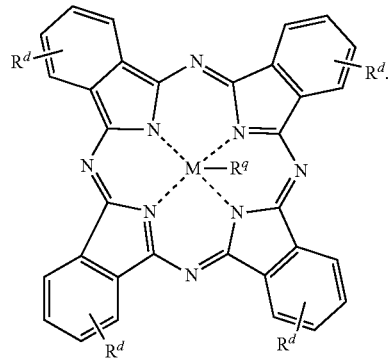

22. The process of claim 1, wherein the precursor to the Lewis acid is

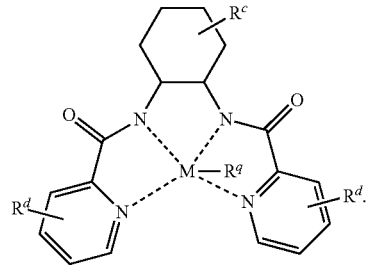

23. The process of claim 1, wherein the precursor to the Lewis acid is

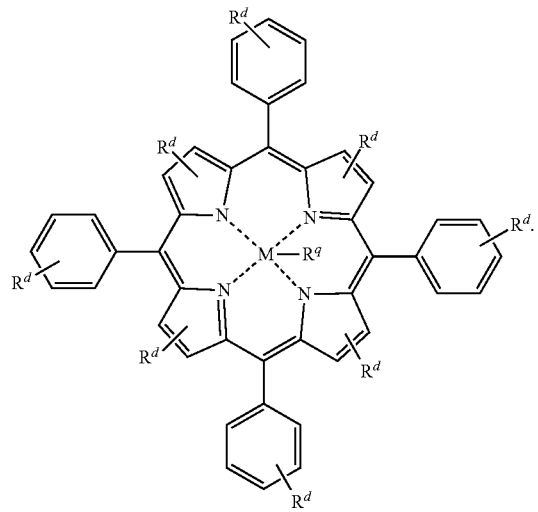

24. The process of claim 1, wherein the precursor to the Lewis acid is

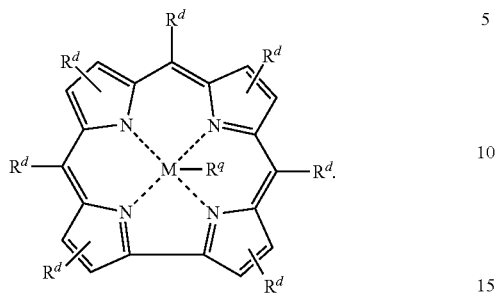

25. The process of claim 1, wherein M is aluminum, chromium, titanium, indium, gallium, zinc, cobalt, or copper.

26. The process of claim 1, wherein M is aluminum or chromium.

27. The process of claim 1, wherein the catalyst replacement components have a halide content less than about 200 ppm.

28. A process for continuous carbonylation of an epoxide or lactone feedstock, comprising:

continuously reacting an epoxide or lactone feedstock with carbon monoxide in the presence of a carbonylation catalyst in a carbonylation reaction vessel to produce a carbonylation product stream, wherein the carbonylation catalyst comprises a Lewis acid and a metal carbonyl, wherein the carbonylation product stream comprises at least one carbonylation product, at least some of the Lewis acid and at least some of the metal carbonyl, and wherein at a start time of the process, the carbonylation reaction vessel contains an initial concentration of the Lewis acid and an initial concentration of the metal carbonyl;

separating the carbonylation product stream from the carbonylation reaction vessel by a nanofiltration membrane, wherein the nanofiltration membrane retains at least a portion of the Lewis acid and at least a portion of the metal carbonyl, and permeates at least one carbonylation product; and adding to the carbonylation reaction vessel, at a time after the start time of the process, a catalyst replacement component which is different from the carbonylation catalyst, wherein the catalyst replacement component is added at a rate or time of addition based on a rate of depletion of one or both of the Lewis acid and the metal carbonyl in the carbonylation reaction vessel, wherein the catalyst replacement component comprises the Lewis acid, a precursor to the Lewis acid, the metal carbonyl, and a precursor to the metal carbonyl, wherein the precursor to the metal carbonyl is a neutral metal carbonyl complex, and wherein the precursor to the Lewis acid is:

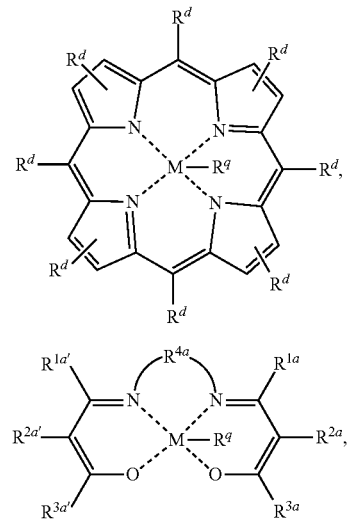

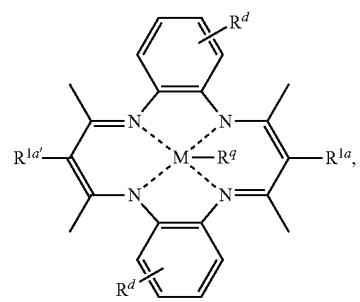

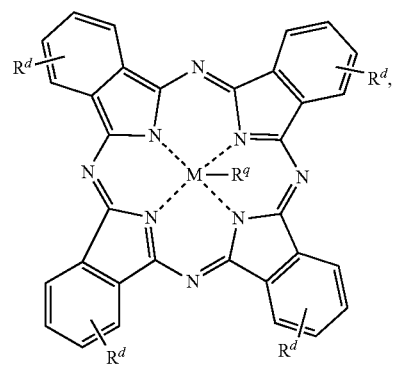

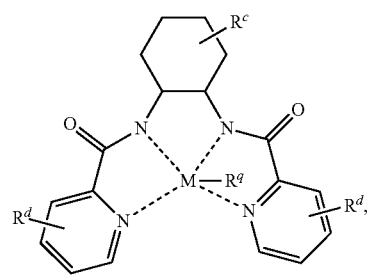

-continued

[porphyrin structures with M—R^q center and R^d substituted phenyl groups]

wherein:
each $R^q$ is independently $C_{1-12}$ aliphatic or aryl, wherein the aryl is unsubstituted or substituted with one or more substituents selected from the group consisting of halogen; —$(CH_2)_{0-4}R°$; —$(CH_2)_{0-4}OR°$; —O—$(CH_2)_{0-4}C(O)OR°$; —$(CH_2)_{0-4}$ $CH(OR°)_2$; —$(CH_2)_{0-4}SR°$; —$(CH_2)_{0-4}Ph$; —$(CH_2)_{0-4}$ $O(CH_2)_{0-1}Ph$; —CH=CHPh; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)N(R°)_2$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR°$; —SC(S)SR°; —$(CH_2)_{0-4}SC(O)R°$; —$(CH_2)_{0-4}C(O)NR°_2$; —$C(S)NR°_2$; —$C(S)SR°$, —SC(S)SR°; —$(CH_2)_{0-4}OC(O)NR°_2$; —C(O)N(OR°)R°, —C(O)C(O)R°, —C(O)$CH_2$C(O)R°; —C(NOR°)R°; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —N(OR°)R°; —C(NH)NR°_2; —P(O)_2R°; —P(O)R°_2; —OP(O)R°_2; —OP(O)(OR°)_2; SiR°_3; —$(C_{1-4}$ straight or branched alkylene)O—N(R°)_2; and —$(C_{1-4}$ straight or branched alkylene)C(O)O—N(R°)_2,
wherein R° at each occurrence is
independently hydrogen, $C_{1-8}$ aliphatic, —$CH_2Ph$, or —$O(CH_2)_{0-1}Ph$; or
a 5-6-membered saturated, partially unsaturated, or aryl ring having 0-4 heteroatoms independently selected from nitrogen, oxygen, and sulfur; or
wherein two independent occurrences of R°, taken together with their intervening atom(s), form a 3-12-membered saturated, partially unsaturated, or aryl mono- or polycyclic ring having 0-4 heteroatoms independently selected from nitrogen, oxygen, and sulfur;

M is a metal atom;

$R^d$ at each occurrence is
independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, or —$SiR^y_3$; or an optionally substituted group selected from the group consisting of:
$C_{1-20}$ aliphatic;
$C_{1-20}$ heteroaliphatic having 1-4 heteroatoms independently selected from the group consisting of nitrogen, oxygen, and sulfur;
6- to 10-membered aryl;
5- to 10-membered heteroaryl having 1-4 heteroatoms independently selected from nitrogen, oxygen, and sulfur; and
4- to 7-membered heterocyclic having 1-2 heteroatoms independently selected from the group consisting of nitrogen, oxygen, and sulfur; or
wherein two or more $R^d$ groups may be taken together to form one or more optionally substituted rings;

each $R^y$ is
independently hydrogen; or an optionally substituted group selected the group consisting of:
acyl;
carbamoyl,
arylalkyl;
6- to 10-membered aryl;
$C_{1-12}$ aliphatic;
$C_{1-12}$ heteroaliphatic having 1-2 heteroatoms independently selected from the group consisting of nitrogen, oxygen, and sulfur;
5- to 10-membered heteroaryl having 1-4 heteroatoms independently selected from the group consisting of nitrogen, oxygen, and sulfur;
4- to 7-membered heterocyclic having 1-2 heteroatoms independently selected from the group consisting of nitrogen, oxygen, and sulfur;
an oxygen protecting group; and
a nitrogen protecting group; or
wherein two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each $R^4$ is independently a hydroxyl protecting group or $R^y$;

$R^{1a}$, $R^{1a'}$, $R^{2a}$, $R^{2a'}$, $R^{3a}$, and $R^{3a'}$ are
independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, or —$SiR^y_3$; or an optionally substituted group selected from the group consisting of:
$C_{1-20}$ aliphatic;
$C_{1-20}$ heteroaliphatic having 1-4 heteroatoms independently selected from the group consisting of nitrogen, oxygen, and sulfur;
6- to 10-membered aryl;
5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; or wherein any of ($R^{2a'}$ and $R^{3'}$), ($R^{2a}$ and $R^{3a}$), ($R^{1a}$ and $R^{2a}$), and ($R^{1a'}$ and $R^{2'}$) may optionally be taken together with the carbon atoms to which they are attached to form one or more rings which may in turn be substituted with one or more $R^y$ groups; and $R^{4a}$ is selected from the group consisting of:

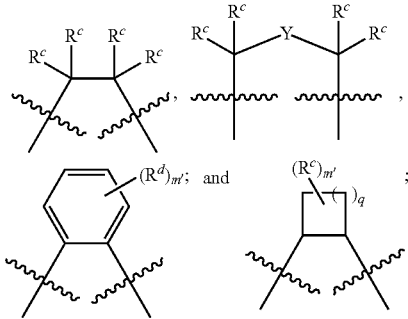

wherein:

$R^c$ at each occurrence is independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, or —$SiR^y_3$; or an optionally substituted group selected from the group consisting of:

$C_{1-20}$ aliphatic;

$C_{1-20}$ heteroaliphatic having 1-4 heteroatoms independently selected from the group consisting of nitrogen, oxygen, and sulfur;

6- to 10-membered aryl;

5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; or wherein two or more $R^c$ groups may be taken together with the carbon atoms to which they are attached and any intervening atoms to form one or more rings; or wherein two $R^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;

Y is a divalent linker selected from the group consisting of: —$NR^y$—, —$N(R^y)C(O)$—, —$C(O)NR^y$—, —O—, —C(O)—, —OC(O)—, —C(O)O—, —S—, —SO—, —$SO_2$—, —C(=S)—, —C(=$NR^y$)—, —N=N—; a polyether; a $C_3$ to $C_8$ substituted or unsubstituted carbocycle; and a $C_1$ to $C_8$ substituted or unsubstituted heterocycle;

m' is 0 or an integer from 1 to 4, inclusive; and q is 0 or an integer from 1 to 4, inclusive.

29. The process of claim 1, wherein each $R^q$ is independently $C_{1-12}$ aliphatic.

30. The process of claim 14, wherein each $R^q$ is independently $C_{1-12}$ aliphatic.

31. The process of claim 28, wherein each $R^q$ is independently $C_{1-12}$ aliphatic.

* * * * *